(12) United States Patent
Graham et al.

(10) Patent No.: US 12,365,678 B2
(45) Date of Patent: Jul. 22, 2025

(54) PHARMACEUTICAL PROCESS FOR THE PREPARATION OF 4-{4-[(3R)-3-METHYLMORPHOLIN-4-YL]-6-[1-((R)-S-METHYLSULFONIMIDOYL) CYCLOPROPYL]PYRIMIDIN-2-YL}-1H-PYRROLO[2,3-B] PYRIDINE AND INTERMEDIATES

(71) Applicant: AstraZeneca AB, Södertälje (SE)

(72) Inventors: Mark Andrew Graham, Cambridge (GB); Lucinda Victoria Jackson, Cambridge (GB); Gary Michael Noonan, Cambridge (GB); Phillip Anthony Inglesby, Cambridge (GB); David Pranay Dave, Cambridge (GB); Katie Grace Cooper, Cambridge (GB)

( * ) Notice: Subject to any disclaimer, the term of this patent is extended or adjusted under 35 U.S.C. 154(b) by 918 days.

(21) Appl. No.: 17/415,110

(22) PCT Filed: Dec. 17, 2019

(86) PCT No.: PCT/EP2019/085568
§ 371 (c)(1),
(2) Date: Jun. 17, 2021

(87) PCT Pub. No.: WO2020/127208
PCT Pub. Date: Jun. 25, 2020

(65) Prior Publication Data
US 2022/0056027 A1 Feb. 24, 2022

Related U.S. Application Data

(60) Provisional application No. 62/780,993, filed on Dec. 18, 2018, provisional application No. 62/859,259, filed on Jun. 10, 2019.

(51) Int. Cl.
| C07D 471/04 | (2006.01) |
| B01J 31/02 | (2006.01) |
| B01J 31/22 | (2006.01) |
| B01J 31/24 | (2006.01) |
| B01J 35/39 | (2024.01) |
| C07C 255/58 | (2006.01) |
| C12P 17/16 | (2006.01) |

(52) U.S. Cl.
CPC ........ *C07D 471/04* (2013.01); *B01J 31/0235* (2013.01); *B01J 31/2226* (2013.01); *B01J 31/2409* (2013.01); *B01J 35/39* (2024.01); *C07C 255/58* (2013.01); *C12P 17/16* (2013.01); *B01J 2531/824* (2013.01)

(58) Field of Classification Search
CPC .................................................. C07D 471/04
See application file for complete search history.

(56) References Cited

U.S. PATENT DOCUMENTS

| 8,252,802 B2 * | 8/2012 | Foote ................... A61K 31/505 514/258.1 |
| 8,552,004 B2 * | 10/2013 | Foote ................... C07D 471/04 514/258.1 |
| 8,999,997 B2 * | 4/2015 | Foote ..................... A61P 43/00 514/258.1 |
| 9,155,742 B2 * | 10/2015 | Foote ................... A61K 31/505 |
| 9,421,213 B2 * | 8/2016 | Foote ................. A61K 31/5377 |
| 2015/0246897 A1 | 9/2015 | Dietmar et al. |

FOREIGN PATENT DOCUMENTS

| WO | 2011154737 A1 | 12/2011 |
| WO | 2012/115478 A2 | 8/2012 |
| WO | 2016202251 A1 | 12/2016 |
| WO | 2017068412 A1 | 4/2017 |

OTHER PUBLICATIONS

Foote et.al. J. Med. Chem. 2018, 61, 9889-9907 (Year: 2018).*

(Continued)

*Primary Examiner* — John S Kenyon
*Assistant Examiner* — Rehana Ismail

(57) ABSTRACT

The present disclosure concerns the large-scale manufacture of pharmaceutical compounds, and novel intermediates for use in the manufacture. International Patent Application WO2011154737 discloses morpholine pyrimidines useful for treating cancer, processes for their preparation and pharmaceutical compositions thereof. In particular, WO2011154737 discloses, as experimental Example 2.02 on page 60, the compound 4-{4-[(3R)-3-methylmorpholin-4-yl]-6-[1-((R)—S-methylsulfonimidoyl)cyclopropyl]pyrimidin-2-yl}-1H-pyrrolo[2,3-b]pyridine (hereafter referred to as the compound of Formula (I)). The structure of the compound of Formula (I) is shown below. A synthetic route to the compound of Formula (I) is described at pages 51 to 57, 66 and 67 of WO2011154737, and is summarised below in Scheme 1.

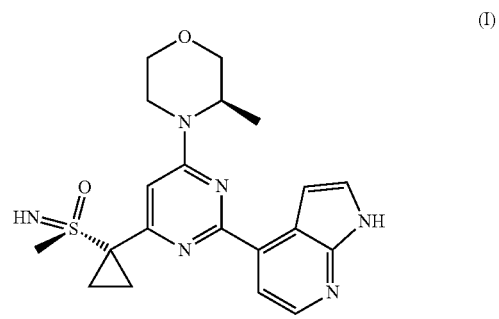

(I)

22 Claims, No Drawings

(56) References Cited

OTHER PUBLICATIONS

Foote, K. M., et al. Journal of Medicinal Chemistry "Discovery of 4-{4-[(3R)-3 Methylmorpholin-4-yl]-6-[1(methylsulfonyl) cyclopropyl]pyrimidin 2-yl}-1H-indole (AZ20): A Potent and Selective Inhibitor of ATR Protein Kinase with Monotherapy in Vivo Antitumor Activity" Feb. 11, 2013.

Foote et al., Discovery and Characterization of AZD6738, a Potent Inhibitor of Ataxia Telangiectasia Mutated and Rad3 Related (ATR) Kinase with Application as an Anticancer Agent, J. Med. Chem., 2018, vol. 61, pp. 9889-9907.

Goundry et al., Development and Scale-up of a Biocatalytic Process to Form a Chiral Sulfoxide, Org. Process. Res. Dev., 2017, vol. 21, pp. 107-113.

Lennox et al., Selection of boron reagents for Suzuki-Miyaura coupling, Chem. Soc. Rev., 2014, vol. 43, pp. 412-443.

Maczka, et al., Biotechnological Methods of Sulfoxidation: Yesterday, Today, Tomorrow, Catalysts, 2018, vol. 8, p. 624.

Murarka, N-(Acyloxy)phthalimides as Redox-Active Esters in Cross-Coupling Reactions, Adv. Synth. Catal., 2018, vol. 360, pp. 1735-1753.

PCT/EP2019/085568 International Search Report and Written Opinion mailed Jul. 29, 2020.

\* cited by examiner

PHARMACEUTICAL PROCESS FOR THE PREPARATION OF 4-{4-[(3R)-3-METHYLMORPHOLIN-4-YL]-6-[1-((R)-S-METHYLSULFONIMIDOYL)CYCLOPROPYL]PYRIMIDIN-2-YL}-1H-PYRROLO[2,3-B] PYRIDINE AND INTERMEDIATES

CROSS-REFERENCE TO RELATED APPLICATIONS

This application is a U.S. National Stage Application of International Application No. PCT/EP2019/085568, filed on Dec. 17, 2019, which claims the benefit under 35 U.S.C. § 119 (e) of U.S. Provisional Application No. 62/780,993, filed Dec. 18, 2018, and U.S. Provisional Application No. 62/859,259, filed Jun. 10, 2019. Each of the above listed applications is incorporated by reference in its entirety for all purposes.

The present disclosure concerns the large-scale manufacture of pharmaceutical compounds, and novel intermediates for use in the manufacture.

International Patent Application WO2011154737 discloses morpholino pyrimidines useful for treating cancer, processes for their preparation and pharmaceutical compositions thereof. In particular, WO2011154737 discloses, as experimental Example 2.02 on page 60, the compound 4-{4-[(3R)-3-methylmorpholin-4-yl]-6-[1-((R)—S-methyl-sulfonimidoyl)cyclopropyl]pyrimidin-2-yl}-1H-pyrrolo[2,3-b]pyridine (hereafter referred to as the compound of Formula (I)). The structure of the compound of Formula (I) is shown below.

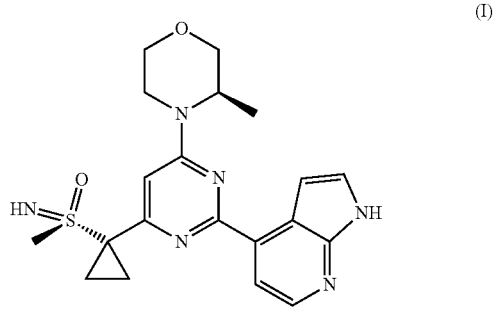 [SMILES: C[C@@H]1COCCN1c1cc(C2([S@](C)(=N)=O)CC2)nc(-c2ccnc3[nH]ccc23)n1]

A synthetic route to the compound of Formula (I) is described at pages 51 to 57, 66 and 67 of WO2011154737, and is summarised below in Scheme 1.

Scheme 1

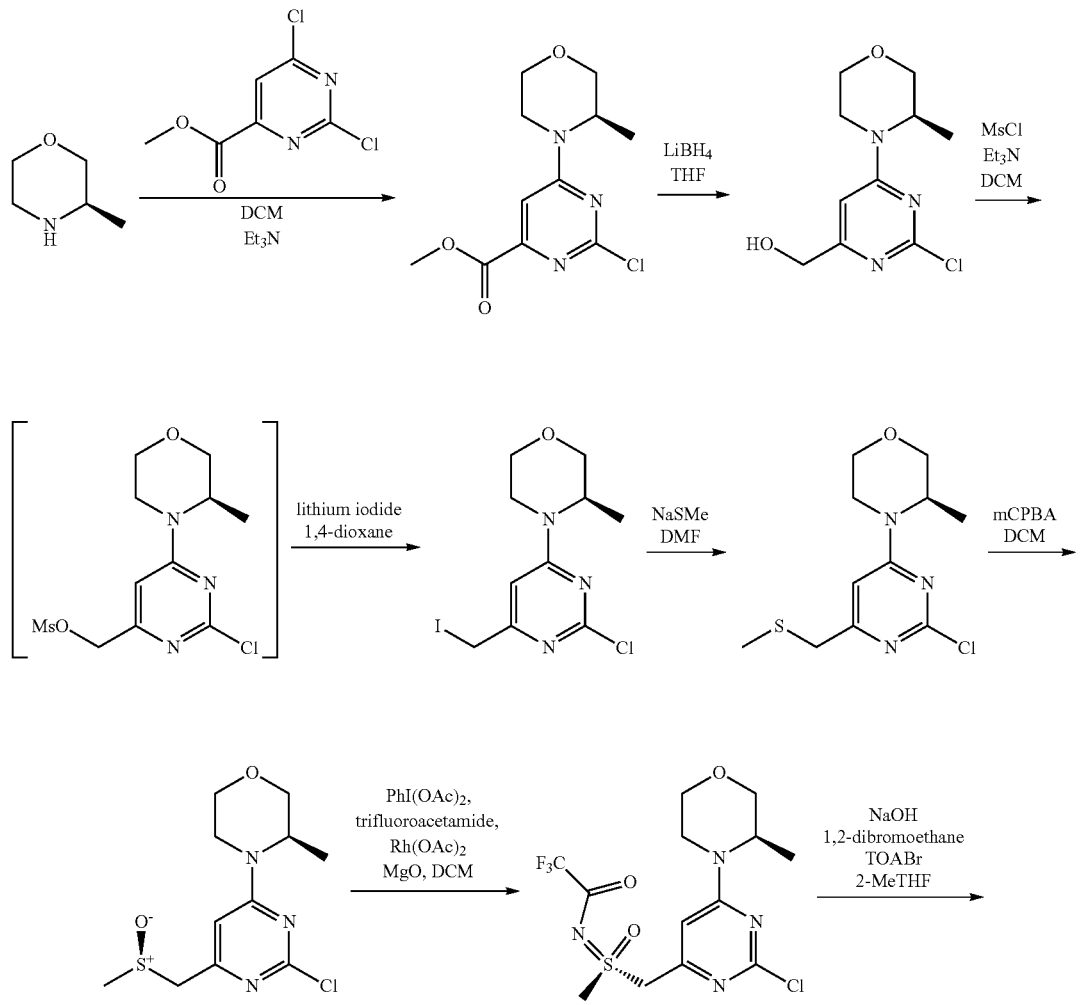

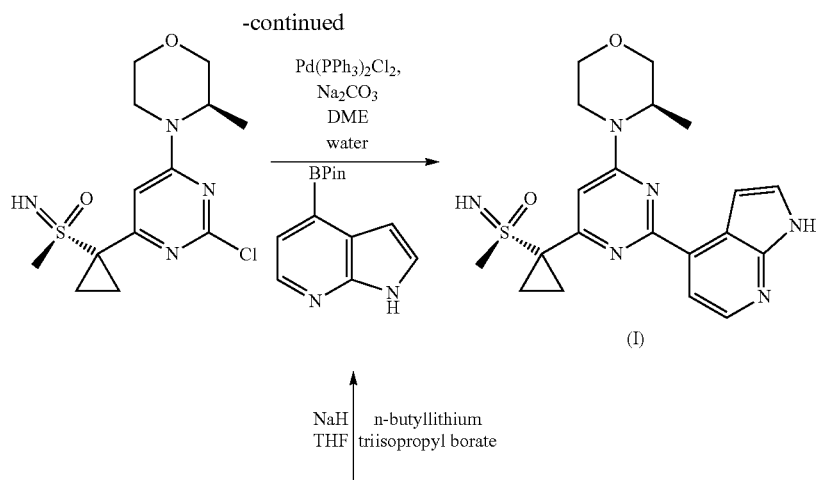

(I)

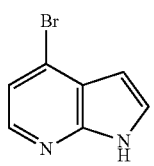

The route to the compound of Formula (I) as shown in Scheme 1 has a number of potential disadvantages. For example, Scheme 1 has a total of 15 stages (there is a 5 step synthesis to obtain the starting compound (R)-3-methylmorpholine, although this compound is also commercially available) and the scheme is not convergent, with the longest linear sequence being made up of 14 stages, which on a commercial scale may be undesirable. In addition, the cyclopropanation step is very challenging, requiring a continuous stirred tank process with a challenging work up and only a moderate yield with many impurities formed. Introduction of the reactive sulfoximine early in the scheme also causes significant issues with subsequent cyclopropanation and Suzuki coupling. The scheme also requires the early introduction of the expensive chiral morpholine. Furthermore, the use of rhodium in the sulfoximine formation stage can be expensive. Taken together or in isolation, these potential disadvantages may render the route as shown in Scheme 1 unattractive for use on a commercial scale at reasonable cost.

The compound of Formula (I) is being developed as an active pharmaceutical compound for the treatment of cancer. Appropriate methods for safe, cost-effective, efficient and environmentally sensitive manufacture of the compound of Formula (I) may therefore be desirable. Given the potential disadvantages highlighted above, it is desirable to develop a shorter route, i.e. with fewer stages, which is more efficient and economical.

Applicants have now found a route to the synthesis of a key cyclopropyl intermediate of Formula (II), as described in Scheme 2 below, wherein LG¹ is a leaving group.

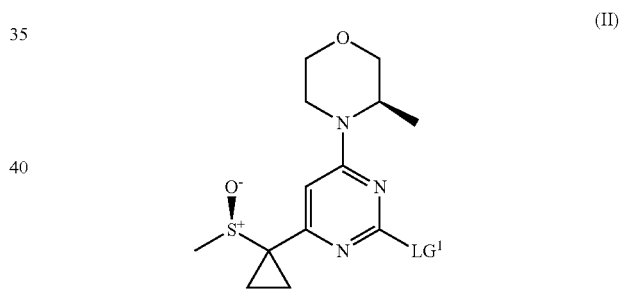

In a first aspect of the disclosure, therefore, there is provided a process for preparing a compound of Formula (II), wherein LG$^1$ is a leaving group, comprising the asymmetric sulphur oxidation of a compound of Formula (III) by reacting with an oxidative enzyme (Scheme 2).

Scheme 2

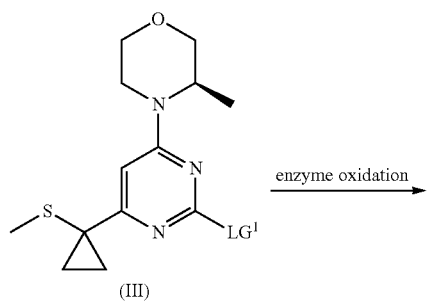

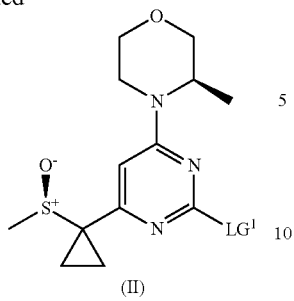

(II)

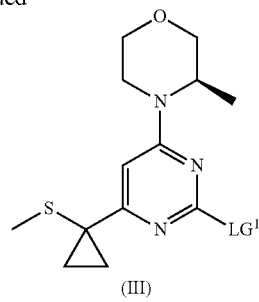

(III)

As used herein, the group LG$^1$ is selected from chlorine, bromine and triflate (also known as trifluoromethanesulfonate). In one embodiment, LG$^1$ is chlorine. In one embodiment, LG$^1$ is bromine or triflate.

The reaction may be performed using a suitable oxidative enzyme, for example a mono-oxygenase enzyme, such as a Baeyer-Villiger mono-oxygenase (BVMO) or a cyclohexanone mono-oxygenase (CHMO) enzyme. CHMO enzymes are considered in the art to be a subset of BVMO enzymes. In one embodiment, the oxidative enzyme is cyclohexanone mono-oxygenase. The reaction is carried out in the presence of oxygen.

An enzyme co-factor may also be used for this reaction, such as nicotinamide adenine dinucleotide (NAD) or nicotinamide adenine dinucleotide phosphate (NADP). In one embodiment, the enzyme co-factor is nicotinamide adenine dinucleotide phosphate.

A co-enzyme can be used for recycling the co-factor such as keto-reductase, which is familiar to those skilled in the art.

The reaction may be performed in a water and a water-miscible organic solvent. Suitable water-miscible organic solvents include isopropyl alcohol or tetrahydrofuran. In one embodiment, the solvent comprises isopropyl alcohol and water.

The reaction may be carried out at a range of temperatures, for example 10° C. to 50° C. In one embodiment, the reaction is carried out between 25° C. and 35° C. The reaction may be carried out at a range of pH, such as from pH 7 to pH 10. In a further embodiment, the reaction is performed at pH 8, using a potassium phosphate buffer, for example potassium biphosphate.

In another aspect of the disclosure, there is provided a process for preparing a compound of Formula (III), where LG$^1$ and LG$^2$ are both leaving groups, comprising reacting the compound of Formula (IV) with (R)-3-methylmorpholine, or a salt thereof, in the presence of a base and suitable solvent (Scheme 3).

Scheme 3

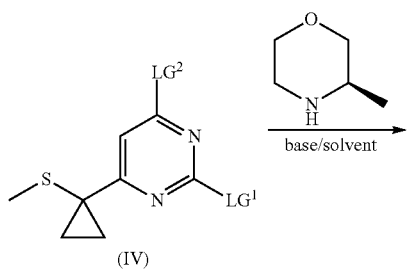

(IV)

The groups LG$^1$ and LG$^2$ are independently selected from chlorine, bromine and triflate. In one embodiment, LG$^1$ and LG$^2$ are both chlorine.

(R)-3-methylmorpholine may be used as either a salt or the free base. In one embodiment, (R)-3-methylmorpholine hydrochloride salt is used.

The reaction may be carried out in a variety of organic solvents such as acetonitrile, dimethylsulfoxide, N,N-dimethylformamide, tetrahydrofuran and toluene. In one embodiment, the solvent comprises dimethylsulfoxide.

The reaction may be carried out using a variety of bases such as potassium carbonate, triethylamine, N,N-diisopropylethylamine or combinations thereof. In one embodiment, the base comprises a mixture of potassium carbonate and triethylamine.

The reaction may be carried out at a range of temperatures, for example 0° C. to 100° C. In one embodiment, the reaction is carried out between 15° C. to 25° C.

In another aspect of the disclosure, there is provided a process for preparing a compound of Formula (IV), comprising reacting the compound of Formula (V) with a suitable activating reagent in the presence of a base (Scheme 4).

Scheme 4

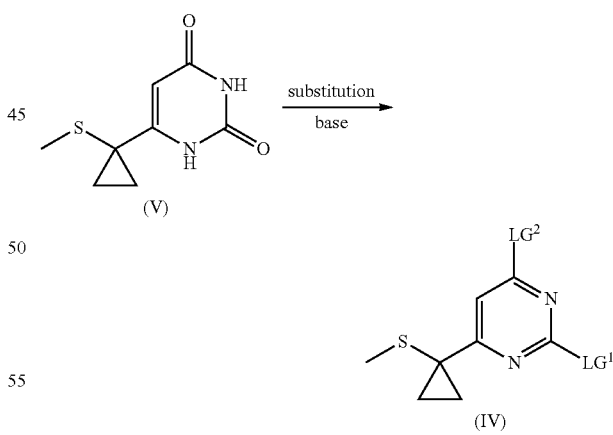

The groups LG$^1$ and LG$^2$ are independently selected from chlorine, bromine and triflate. In one embodiment, LG$^1$ and LG$^2$ are both chlorine.

The reaction may be carried out using a variety of bases such as N,N-diethylaniline, N,N-diisopropylethylamine and triethylamine. In one embodiment, the base is N,N-diethylaniline.

The activating reagent used for substitution will depend on the group selected for LG$^1$ and LG$^2$. The skilled person will be able to select a suitable activating reagent depending on the identity of LG$^1$ and LG$^2$. For example, when LG$^1$ and LG$^2$ are both chlorine, the activating reagent will be a chlorinating agent. Suitable chlorinating agents include phosphoryl chloride, phosphonic dichloride and phosphorous pentachloride, which is used in excess. In one embodiment, where LG$^1$ and LG$^2$ are both chlorine, the chlorinating agent is phosphoryl chloride.

The reaction may be carried out using a variety of co-solvents such as toluene, acetonitrile and chlorobenzene. Alternatively, the reaction may be carried out in neat chlorinating reagent in the presence of base.

The reaction may be carried out at a range of temperatures, for example 50° C. to 140° C. In one embodiment, the reaction is carried out between 90° C. to 110° C.

During the work up any unreacted activating agent, such as phosphoryl chloride, may be quenched by addition to an aqueous solution. The pH may be controlled by quenching the reaction in, for example, aqueous sodium acetate with the simultaneous addition of sodium hydroxide. Maintaining the pH within the range of 5 to 7 has the advantage of reducing decomposition of the product of Formula (IV).

In another aspect of the disclosure, there is provided a process for preparing a compound of Formula (V), from a compound of Formula (VI) (Scheme 5).

Scheme 5

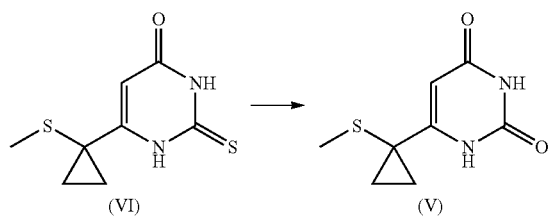

(VI)  (V)

The reaction may be carried out using a variety of reagents. Suitable reagents for converting a thiopyrimidone to a pyrimidone will be familiar to those skilled in the art and include, for example, chloroacetic acid, iodosobenzene or oxone. In one embodiment, the reagent is chloroacetic acid.

The reaction may be carried out in a variety of solvents such as methanol, ethanol, water, 1,4-dioxane and tetrahydrofuran. In one embodiment, the solvent is water. Additional acids such as hydrochloric acid or acetic acid may be used for this transformation.

The reaction may be carried out at a range of temperatures, for example 20° C. to 120° C. In one embodiment, the reaction is carried out between 90° C. to 100° C.

In another aspect of the disclosure, there is provided a process for preparing a compound of Formula (VI), comprising reacting a compound of Formula (VII) with thiourea (Scheme 6).

Scheme 6

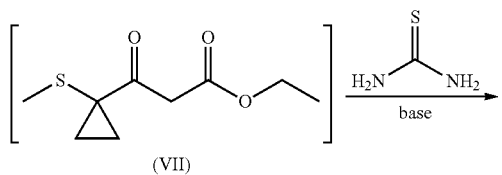

(VII)

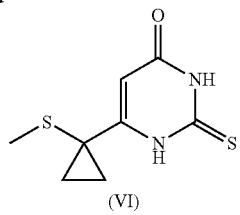

(VI)

The reaction with thiourea may be carried out in the presence of a base. The base may be an inorganic base, for example, sodium hydroxide or metal alkoxides such as sodium methoxide, sodium ethoxide, sodium tert-butoxide or potassium salts thereof. In one embodiment, the base comprises sodium ethoxide. In another embodiment, the base comprises potassium tert-butoxide. In yet another embodiment, thiourea is replaced with urea. In at least one embodiment, thiourea is used.

The reaction may be carried out in a variety of organic solvents, such as methanol, ethanol, isopropanol, tetrahydrofuran, 2-methyltetrahydrofuran and acetonitrile. In one embodiment, the solvent comprises ethanol.

The reaction may be carried out at a range of temperatures, for example 50° C. to 120° C. In one embodiment, the reaction is carried out between 70° C. to 85° C., such as 75 to 80° C.

In another aspect of the disclosure, there is provided a process for preparing a compound of Formula (VII), comprising acylation of a malonate derivative with an activated form of the compound of Formula (VIII), followed by decarboxylation (Scheme 7).

Scheme 7

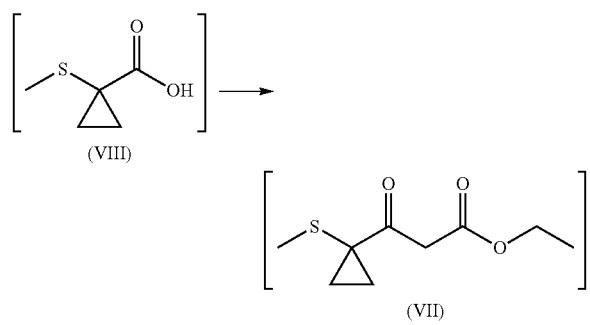

The reaction may be carried out in a variety of organic solvents such as ethyl acetate, dichloromethane, tetrahydrofuran, 2-methyltetrahydrofuran and acetonitrile. In one embodiment, the solvent comprises 2-methyltetrahydrofuran.

Coupling reagents suitable for generating the active species will be familiar to those skilled in the art and include carbonyldiimidazole, thionyl chloride, oxalyl chloride or isobutyl chloroformate. In one embodiment, carbonyldiimidazole is used as the coupling reagent.

Suitable reagents for making the beta-keto ester will be familiar to those skilled in the art and include ethyl potassium malonate or Meldrum's acid. In one embodiment, the agent is ethyl potassium malonate.

The reaction may be performed using a variety of bases such as triethylamine, N,N-diisopropylethylamine, potassium carbonate or potassium hydroxide. In one embodiment, the base is triethylamine.

The reaction may be performed using a salt additive to enhance the decarboxylation. In one embodiment, the additive is magnesium chloride.

The reaction may be carried out at a range of temperatures, for example 0° C. to 80° C. In one aspect, the reaction is carried out between 10° C. to 40° C.

In another aspect of the disclosure, there is provided a process for preparing a compound of Formula (VIII), comprising the thiomethylation and base-induced cyclisation of a compound of Formula (IX) followed by hydrolysis (Scheme 8).

Scheme 8

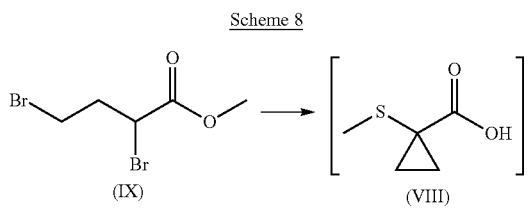

(IX)    (VIII)

The reaction may be carried out in a variety of organic solvents such as methanol, tetrahydrofuran, 2-methyltetrahydrofuran, dichloromethane and acetonitrile or a mixture of solvents. In one embodiment, the solvent comprises a mixture of 2-methyltetrahydrofuran and methanol.

The first stage of this reaction involves nucleophilic substitution of bromine with thiomethoxide. The reaction may be carried out using a variety of thiomethoxide salts. In one embodiment, the thiomethoxide salt is sodium thiomethoxide.

The reaction may be carried out using a variety of bases such as sodium hydroxide or metal alkoxides such as sodium methoxide, sodium ethoxide, sodium tert-butoxide or potassium salts thereof. In one embodiment, the base is sodium methoxide.

The hydrolysis stage may be carried out by methods which will be familiar to those skilled in the art. A variety of aqueous bases or acids may be used such as sodium hydroxide, potassium hydroxide or hydrochloric acid. In one embodiment, the base for hydrolysis is sodium hydroxide.

The reaction may be carried out at a range of temperatures, for example 0° C. to 80° C. In one embodiment, the reaction is carried out between 10° C. to 25° C.

The product may be crystallised or telescoped through to the next stage as a solution in organic solvent. In one embodiment, the product is telescoped as a 2-methyltetrahydrofuran solution.

Further to the synthetic routes described above, Applicants have found an alternative route for the synthesis of the compound of Formula (IV) from the compound of Formula (VIII) which cuts down the four-stage process described above (Schemes 4 to 7) to two stages, which are represented in Schemes 9 and 10 below. Incorporation of this alternative route in the manufacture of the compound of Formula (I) means that the overall length is 8 stages with the longest linear sequence being only 7 stages. This shortened manufacturing route further improves the efficiency and cost-effective manufacture of the compound of Formula (I) and is more environmentally sustainable due to the reduced amount of resource and waste.

Therefore, in an alternative aspect of the disclosure, there is provided a process for preparing a compound of Formula (IV), comprising reacting a compound of Formula (XIII) with a 2,4-difunctionalised pyrimidine in the presence of light and a photo-catalyst (Scheme 9).

Scheme 9

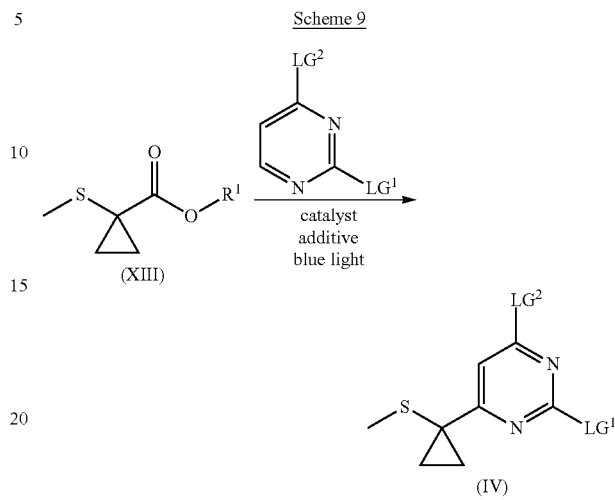

The groups $LG^1$ and $LG^2$ are each independently selected from chlorine, bromine and triflate. In one embodiment, $LG^1$ and $LG^2$ are both chlorine.

The group $R^1$ is a group which is suitable for fragmentation and decarboxylation under photoredox conditions. Suitable groups will be known to the skilled person and include phthalimide and tetrachlorophthalimide. In one embodiment, $R^1$ is phthalimide and therefore the compound of Formula (XIII) may be represented as a compound of Formula (XIIIa):

(XIIIa)

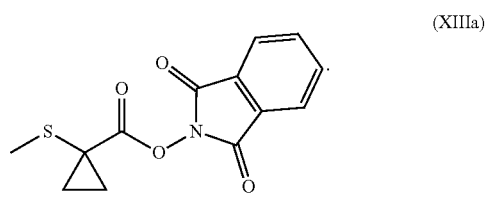 [SMILES: CSC1(C(=O)ON2C(=O)c3ccccc3C2=O)CC1]

In one embodiment, the functionalised pyrimidine is selected from 2,4-dichloropyrimidine, 2,4-dibromopyrimidine and 2,4-pyrimidinediyl bis(trifluoromethanesulfonate). In one embodiment, the 2,4-difunctionalised pyrimidine is 2,4-dichloropyrimidine.

The reaction may be carried out using a variety of photo-catalysts such as 4,4'-di-tert-butyl-2,2'-bipyridine)bis[(2-pyridinyl)phenyl]iridium(III) hexafluorophosphate, bis [2-(2,4-difluorophenyl)-5-trifluoromethylpyridine][2-2'-bipyridyl]iridium hexafluorophosphate, 2,4,5,6-tetra(9H-carbazol-9-yl)isophthalonitrile, 2,4,6-tris(di-4-biphenylylamino)-3,5-difluorobenzonitrile, 2,3,4,5,6-pentakis(3,6-diphenylcarbazol-9-yl)benzonitrile and 2,4,6-tris (diphenylamino)-3,5-difluorobenzonitrile4. In one embodiment, the photo-catalyst is selected from (4,4'-di-tert-butyl-2,2'-bipyridine)bis[(2-pyridinyl)phenyl]iridium (III) hexafluorophosphate, bis [2-(2,4-difluorophenyl)-5-trifluoromethylpyridine][2-2'-bipyridyl]iridium hexafluorophosphate and 2,4,5,6-tetra(9H-carbazol-9-yl)isophthalonitrile. In one embodiment, the catalyst is 2,4,5,6-tetra (9H-carbazol-9-yl)isophthalonitrile (4CzIPN).

In one embodiment, the catalyst is a benzonitrile or isophthalonitrile organophoto-catalyst, such as 2,4,5,6-tetra (9H-carbazol-9-yl)isophthalonitrile, 2,4,6-tris(di-4-biphenylylamino)-3,5-difluorobenzonitrile, 2,3,4,5,6-pentakis(3,6-diphenylcarbazol-9-yl)benzonitrile or 2,4,6-tris(diphenylamino)-3,5-difluorobenzonitrile.

In one embodiment, the catalyst is a benzonitrile photocatalyst selected from 2,4,6-tris(di-4-biphenylylamino)-3,5-difluorobenzonitrile, 2,3,4,5,6-pentakis(3,6-diphenylcarbazol-9-yl)benzonitrile and 2,4,6-tris(diphenylamino)-3,5-difluorobenzonitrile. These benzonitrile catalysts have certain advantages over other photo-catalysts, for example, by allowing for a faster rate of reaction which can improve the throughput of the continuous flow process described herein, and improving overall yield. Furthermore, the benzonitrile catalysts described herein do not require use of N,N-diisopropylethylamine (DIPEA) as an additive to improve the rate of reaction. The advantages of not using DIPEA in photoredox reactions will be known to the skilled person and include significantly reduced darkening as well as allowing for a more efficient scale up of the photoredox reaction.

In one embodiment, the catalyst is 2,4,6-tris(di-4-biphenylylamino)-3,5-difluorobenzonitrile. In another embodiment, the catalyst is 2,3,4,5,6-pentakis(3,6-diphenylcarbazol-9-yl)benzonitrile. In another embodiment, the catalyst is 2,4,6-tris(diphenylamino)-3,5-difluorobenzonitrile.

Applicants have identified a novel compound useful as a photo-catalyst. Therefore, in one aspect of the present invention there is provided the compound 2,4,6-tris(di-4-biphenylylamino)-3,5-difluorobenzonitrile:

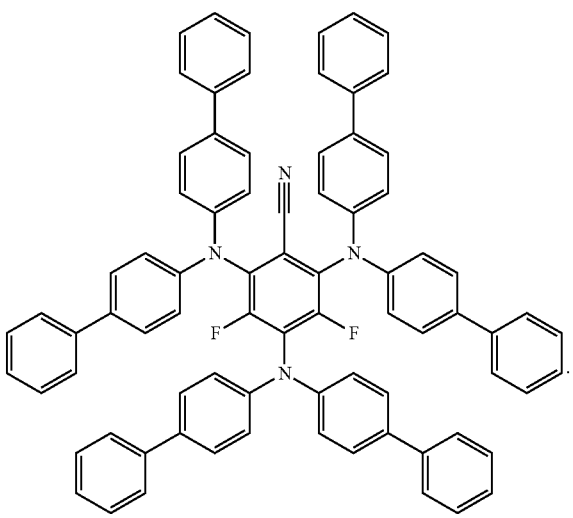 [SMILES: N#Cc1c(N(c2ccc(-c3ccccc3)cc2)c2ccc(-c3ccccc3)cc2)c(F)c(N(c2ccc(-c3ccccc3)cc2)c2ccc(-c3ccccc3)cc2)c(F)c1N(c1ccc(-c2ccccc2)cc1)c1ccc(-c2ccccc2)cc1]

Applicants have further identified that the compound 2,3,4,5,6-pentakis(3,6-diphenylcarbazol-9-yl)benzonitrile, previously only believed to be described for use in LED screen applications (for example, WO2016202251), is useful as a photo-catalyst. Therefore, in a further aspect of the invention there is provided use of the compound 2,3,4,5,6-pentakis(3,6-diphenylcarbazol-9-yl)benzonitrile as a catalyst in photoredox reactions.

Furthermore, 2,4,6-tris(diphenylamino)-3,5-difluorobenzonitrile, which is a known photo-catalyst but which is not believed to have been previously disclosed as catalysing a Minisci reaction, has been found to be useful in the reaction shown in Scheme 9.

A light source providing light of a suitable wavelength for the photo-catalyst is required for this reaction (the reaction shown in Scheme 9), for example, blue light emitting diodes (LEDs).

The reaction may be carried out in a variety of solvents such as N,N-dimethylformamide, dimethylsulfoxide or toluene. In one embodiment, the solvent is dimethylsulfoxide.

The reaction may be carried out using a variety of additives such as acids, Lewis acids, amine bases or other radical donors. Examples of additives include trifluoroacetic acid, malonic acid, indium triflate or N,N-diisopropylethylamine. In one embodiment, the additive is N,N-diisopropylethylamine.

The reaction may be carried out at a range of temperatures, for example 0° C. to 100° C. In one embodiment, the reaction is carried out between 25° C. to 50° C.

The reaction may be carried out as a batch process or a continuous flow process in the presence of light. In one embodiment, the reaction is performed in a continuous flow reactor with a blue LED light source.

In another aspect of the disclosure, there is a process for preparing a compound of Formula (XIII) from a compound of Formula (VIII) in the presence of an activating reagent and base (Scheme 10).

Scheme 10

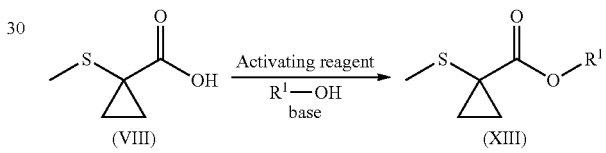

$R^1$ is a group which is suitable for fragmentation and decarboxylation under photoredox conditions. Suitable groups will be known to the skilled person and include phthalimide and tetrachlorophthalimide. In one embodiment, $R^1$—OH is N-hydroxyphthalimide or N-hydroxytetrachlorophthalimide. In one embodiment, $R^1$ is a phthalimide or tetrachlorophthalimide group. When $R^1$—OH is N-hydroxyphthalimide, $R^1$ is a phthalimide group and therefore the compound of Formula (XIII) is represented as a compound of Formula (XIIIa).

The reaction may be carried out in a range of organic solvents such as dichloromethane, tetrahydrofuran and 2-methyltetrahydrofuran. In one embodiment, the reaction is performed in dichloromethane.

The reaction may be carried out using a range of activating reagents to form an acid chloride such as thionyl chloride or oxalyl chloride. In one embodiment, oxalyl chloride is used in the presence of catalytic N,N-dimethylformamide. Alternatively, an activating reagent can be used to form an active ester such as dicyclohexylcarbodiimide, diisopropylcarbodiimide or carbonyldiimidazole.

The reaction may be carried out using a variety of bases such as triethylamine, pyridine or potassium carbonate. In one embodiment, the base is triethylamine.

The reaction may be carried out at a range of temperatures, for example 0° C. to 80° C. In one embodiment, the reaction is carried out between 5° C. to 25° C.

The cyclopropyl intermediate of Formula (II), or salt thereof, synthesized via the methods described herein is a key intermediate in the synthesis of the compound of Formula (I).

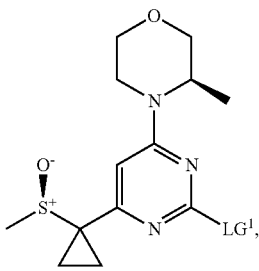

(II)

where LG¹ is a leaving group selected from chlorine, bromine and triflate. In one embodiment, LG¹ is a leaving group selected from bromine and triflate.

In a particular aspect, there is provided the compound (3R)-4-(2-chloro-6-{1-[(R)-methylsulfinyl]cyclopropyl}-4-pyrimidinyl)-3-methylmorpholine, or a salt thereof. In a further aspect, there is provided the compound (3R)-4-(2-chloro-6-{1-[(R)-methylsulfinyl]cyclopropyl}-4-pyrimidinyl)-3-methylmorpholine in free base form.

In a further aspect of the disclosure, there is provided the compound of Formula (III), or a salt thereof.

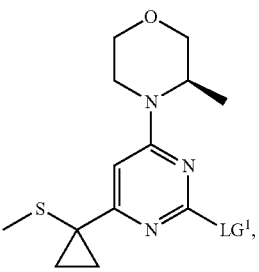

(III)

wherein LG¹ is a leaving group selected from chlorine, bromine and triflate.

In a further aspect, there is provided the compound (3R)-4-{2-chloro-6-[1-(methylsulfanyl)cyclopropyl]-4-pyrimidinyl}-3-methylmorpholine, or a salt thereof. In a further aspect, there is provided the compound (3R)-4-{2-chloro-6-[1-(methylsulfanyl)cyclopropyl]-4-pyrimidinyl}-3-methylmorpholine in free base form.

In a further aspect of the disclosure, there is provided the compound of Formula (IV).

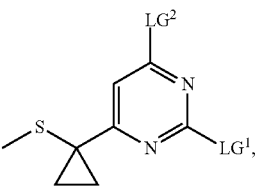

(IV)

wherein LG¹ and LG² are each independently selected from chlorine, bromine and triflate.

In a further aspect, there is provided the compound 2,4-dichloro-6-[1-(methylsulfanyl)cyclopropyl]pyrimidine.

In a further aspect of the disclosure, there is provided the compound of Formula (V), or a salt thereof.

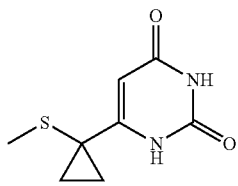

(V)

In a further aspect, there is provided the compound 6-[1-(methylsulfanyl)cyclopropyl]-2,4(1H,3H)-pyrimidinedione, or a salt thereof. In a further aspect, there is provided the compound 6-[1-(methylsulfanyl)cyclopropyl]-2,4(1H,3H)-pyrimidinedione in free base form.

In a further aspect of the disclosure, there is provided the compound of Formula (VI), or a salt thereof.

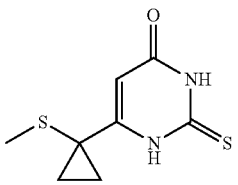

(VI)

In a further aspect, there is provided the compound 6-[1-(methylsulfanyl)cyclopropyl]-2-sulfanylidene-2,3-dihydro-4(1H)-pyrimidinone, or a salt thereof. In a further aspect, there is provided the compound 6-[1-(methylsulfanyl)cyclopropyl]-2-sulfanylidene-2,3-dihydro-4(1H)-pyrimidinone in free base form.

In a further aspect of the disclosure, there is provided the compound of Formula (VII), or a salt thereof.

(VII)

In a further aspect, there is provided the compound ethyl 3-[1-(methylsulfanyl)cyclopropyl]-3-oxopropanoate, or a salt thereof. In a further aspect there is provided the compound 3-[1-(methylsulfanyl)cyclopropyl]-3-oxopropanoate in free base form.

Compounds described in this specification may form acid addition salts or base addition salts. In general, an acid addition salt can be prepared using various inorganic or organic acids. Such salts can typically be formed by, for example, mixing the compound with an acid (e.g., a stoichiometric amount of acid) using various methods known in the art. This mixing may occur in water, an organic solvent (e.g., ether, ethyl acetate, ethanol, isopropanol, or acetonitrile), or an aqueous/organic mixture. An acid addition salt may for example be formed using an inorganic acid selected from the group consisting of hydrochloric acid.

For compounds that may form base addition salts, it may be possible to make, for example, an alkali metal (such as sodium, potassium, or lithium) or an alkaline earth metal (such as a calcium) salt by treating a compound with an alkali metal or alkaline earth metal hydroxide or alkoxide (e.g., an ethoxide or methoxide) or a suitably basic organic amine (e.g., a choline or meglumine) in an aqueous medium.

The general principles and techniques of preparing salts can be found in Berge et al., *J. Pharm. Sci.,* 66, 1-19 (1977).

In one embodiment, there is provided a compound of Formula (I), or salt thereof, which is a single optical isomer being in an enantiomeric excess (% ee) of ≥95%, ≥98% or ≥99%. In one embodiment, the single optical isomer is present in an enantiomeric excess (% ee) of ≥99%.

In one embodiment, there is provided a compound of Formula (II), or a salt thereof, which is a single optical isomer being in an enantiomeric excess (% ee) of ≥95%, ≥98% or ≥99%. In one embodiment, the single optical isomer is present in an enantiomeric excess (% ee) of ≥99%.

In one embodiment, there is provided a compound of Formula (III), or salt thereof, which is a single optical isomer being in an enantiomeric excess (% ee) of ≥95%, ≥98% or ≥99%. In one embodiment, the single optical isomer is present in an enantiomeric excess (% ee) of ≥99%.

In one embodiment, there is provided a compound of Formula (X), or salt thereof, which is a single optical isomer being in an enantiomeric excess (% ee) of ≥95%, ≥98% or ≥99%. In one embodiment, the single optical isomer is present in an enantiomeric excess (% ee) of ≥99%.

In a still further aspect, there is provided the use of any of the compounds of Formula (II), (III), (IV), (V), (VI), (VII), (VIII), (IV) or (XIII), or a salt thereof where applicable, as an intermediate in the manufacture of a compound of Formula (I).

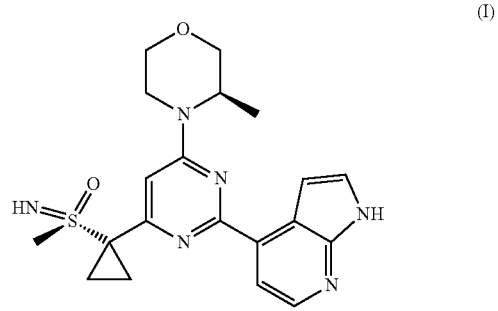 [SMILES: C[C@@H]1COCCN1c1cc(C2([S@](C)(=N)=O)CC2)nc(-c2ccnc3[nH]ccc23)n1]

(I)

The processes described herein provide an alternative route to the compound of Formula (I) which may overcome a number of the problems with previously disclosed routes. For example, reducing the total number of stages, improving the cyclopropanation by, in part, introducing the sulfoximine later in the scheme and removing the need for rhodium in the sulfoximine formation stage.

The general synthetic route to the compound of Formula (I) starting from the compound of Formula (II) is set out below in Scheme 11, wherein $LG^1$ is a leaving group selected from chlorine, bromine and triflate. In one embodiment, $LG^1$ is a leaving group selected from bromine and triflate.

Scheme 11

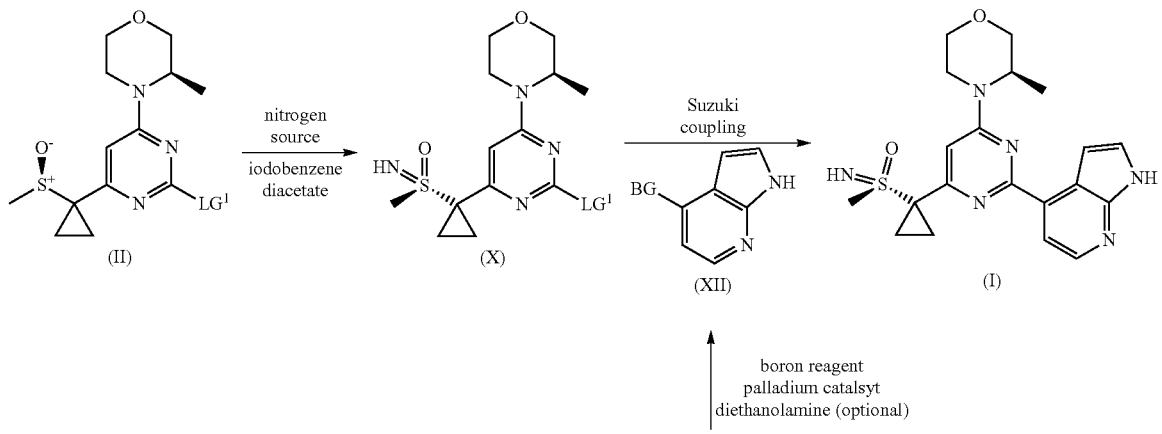

(XI)

In a further aspect of the disclosure, therefore, there is provided a process for preparing the compound of Formula (I) comprising:

(a) reacting a compound of Formula (II) with a nitrogen source and iodobenzene diacetate to form a compound of Formula (X);

(b) reacting a compound of Formula (XI) with a boron reagent in the presence of a palladium catalyst, or following lithium-halogen exchange, and optionally adding diethanolamine, to form a compound of Formula (XII); and (c) cross coupling a compound of Formula (X) with a compound of Formula (XII) to form a compound of Formula (I);

wherein LG$^1$ in the compounds of Formula (II) and Formula (X) is a leaving group selected from chlorine, bromine and triflate; and BG is a boronate ester, such as BPin, the group B(OR)$_2$ where R is hydrogen or a C$_{1-4}$ alkyl, or diethanolamine boronate ester (B(DEA)).

In a further aspect, LG$^1$ in the compounds of Formula (II) and Formula (X) represents chlorine. In one embodiment, LG$^1$ in the compound of Formula (II) and Formula (X) represents bromine or triflate. In a further aspect, BG in the compound of Formula (XII) is BPin. In a further aspect, BG in the compound of Formula (XII) is B(DEA).

The general synthetic route to the compound of Formula (I) starting from the compound of Formula (III) is set out below in Scheme 12, wherein LG$^1$ is a leaving group selected from chlorine, bromine and triflate.

lithium-halogen exchange, and optionally adding diethanolamine, to form a compound of Formula (XII); and (c) cross coupling a compound of Formula (X) with a compound of Formula (XII) to form a compound of Formula (I);

wherein step (a) is preceded by the step of reacting a compound of Formula (III) with an oxidising enzyme to form a compound of Formula (II);

wherein LG$^1$ in the compounds of Formulas (III), (II), and (X) is a leaving group selected from chlorine, bromine and triflate; and BG is a boronate ester, such as BPin, the group B(OR)$_2$ where R is hydrogen or a C$_{1-4}$ alkyl, or diethanolamine boronate ester (B(DEA)).

In a further aspect, LG$^1$ represents chlorine. In a further aspect, BG in the compound of Formula (XII) is BPin. In a further aspect, BG in the compound of Formula (XII) is B(DEA).

As used herein, the term "C$_{1-4}$ alkyl" is a straight or branched chain. Examples of C$_{1-4}$ alkyl are methyl, ethyl, n-propyl, i-propyl, n-butyl, i-butyl, s-butyl or t-butyl, for example, methyl, ethyl, i-propyl or t-butyl.

The following embodiments are described with respect to the aspects relating to Schemes 11 and 12 above.

In one embodiment, step (a) may be carried out using a variety of nitrogen sources such as ammonia, ammonium carbamate and ammonium acetate. In one embodiment, the nitrogen source of step (a) is ammonium carbamate. In a Scheme 12

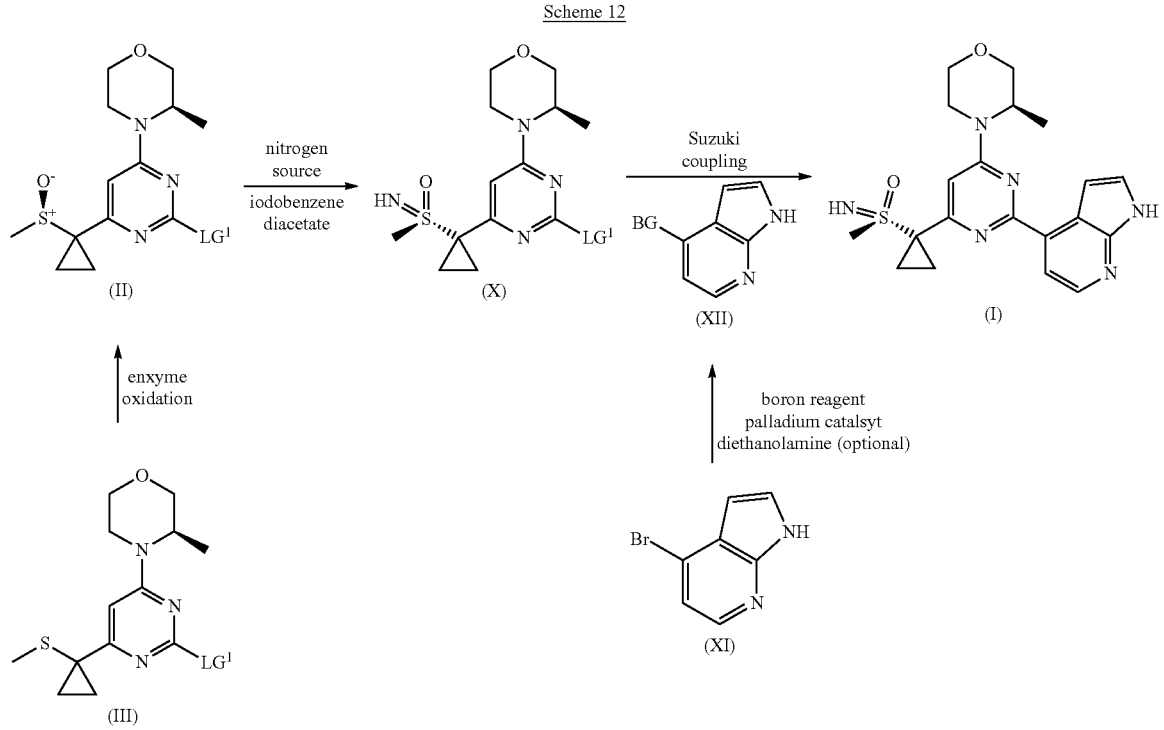

In a further aspect of the disclosure, there is provided a process for preparing the compound of Formula (I) comprising:

(a) reacting a compound of Formula (II) with a nitrogen source and iodobenzene diacetate to form a compound of Formula (X);

(b) reacting a compound of Formula (XI) with a boron reagent in the presence of a palladium catalyst, or following further embodiment, the reaction of step (a) may be carried out in an organic solvent, such as methanol, ethanol, acetonitrile or toluene or a combination thereof. In one embodiment, the organic solvent comprises methanol and toluene. In yet a further aspect, the reaction of step (a) is carried out at between 0° C. to 50° C., for example between 0° C. to 10° C. In a still further aspect, the compound of Formula (X) is isolated as either the free base or the hydrochloride salt. An alternative to step (a), which will be known to those skilled in the art, is to perform the reaction by transfer of trifluoroacetamide, sulphonamide, carbamate or amide using transition metal catalysis followed by hydrolysis. A particular advantage of step (a) is that it avoids the need for an expensive rhodium metal.

In a further embodiment, step (b) may be carried out using a variety of palladium catalysts, such as tetrakis(triphenylphosphine)palladium(O), tris(dibenzylideneacetonyl) bis-palladium, bis(triphenylphosphine)palladium(II) dichloride or palladium acetate with triphenylphosphine. In one embodiment, the palladium catalyst is tetrakis(triphenylphosphine)palladium(O) or tris(dibenzylideneacetonyl) bis-palladium. Other suitable catalysts will be known to those skilled in the art. In one embodiment, the palladium catalyst is tetrakis(triphenylphosphine)palladium(O). In another embodiment, the palladium catalyst is bis(triphenylphosphine)palladium(II) dichloride. In one embodiment, the boron reagent is selected from a bis-boronate ester, such as bis(pinacolato)diboron ($B_2Pin_2$), or the group $B_2(OR)_4$ where R is hydrogen or $C_{1-4}$ alkyl. In one embodiment, the boron reagent is $B_2Pin_2$. In a further embodiment, the reaction is carried out in an organic solvent, such as 1,4-dioxane, 1,2-dimethoxyethane or isopropyl acetate. In one embodiment, the reaction is carried out in an organic solvent, such as 1,4-dioxane or 1,2-dimethoxyethane. In one embodiment, the organic solvent is 1,4-dioxane. In another embodiment, the organic solvent is isopropyl acetate. In yet a further embodiment, the reaction of step (b) may be carried out in the presence of a base, for example potassium carbonate or potassium acetate. In one embodiment, the base is potassium acetate. In a still further embodiment, the reaction of step (b) is carried out at between 90° C. to 100° C.

As described above, in an optional further embodiment, step (b) further comprises the addition of diethanolamine following the reaction with the boron reagent in the presence of the palladium catalyst. The addition of diethanolamine leads to substitution or transesterification of the ester of Formula (XII) and can be done in two different ways. Firstly, in one embodiment, diethanolamine is added to the compound of Formula (XII) where BG is BPin. In one embodiment, the reaction step involving addition of diethanolamine is carried out in the presence of an organic solvent, such as isopropanol or THF or a combination thereof. In one embodiment, the reaction is carried out at room temperature. Secondly, in an alternative embodiment, step (b) is done as a telescopic synthesis starting with the compound of Formula (XI). In this second embodiment, diethanolamine is added to the reaction after the addition of the boron reagent and the palladium catalyst. In one embodiment, the addition of diethanolamine is carried out at a temperature between 20° C. and 80° C., for example 75° C. In one embodiment, when diethanolamine is added as part of a telescopic synthesis, the palladium catalyst is palladium acetate.

When step (b) includes the additional step of diethanolamine addition, the compound of Formula (XII) is a diethanolamine boronic ester, i.e. BG is B(DEA). In one embodiment, the compound of Formula (XII) is a compound of Formula (XIIb):

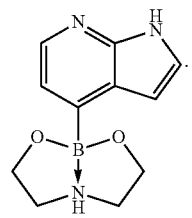

(XIIb)

In a further aspect, step (c) may be carried out using a variety of palladium catalysts such as tetrakis(triphenylphosphine)palladium(O), bis(triphenylphosphine)palladium(II) dichloride or [1,1'-bis(diphenylphosphino)ferrocene]dichloropalladium(II). In one embodiment, the palladium catalyst is [1,1'-bis(diphenylphosphino)ferrocene]dichloropalladium(II). In a further embodiment, the reaction is carried out in an organic solvent such as ethanol, 1-butanol and 2-methyltetrahydrofuran. In one embodiment, the solvent is ethanol. In yet a further embodiment, the reaction of step (c) may be carried out in the presence of a base, for example potassium carbonate, triethylamine or potassium phosphate. In one embodiment, the base is potassium carbonate. In a further embodiment, the reaction of step (c) is carried out between 50° C. to 100° C.

As described in relation to Scheme 12, in one aspect, step (a) is preceded by the step of reacting a compound of Formula (III) with an oxidising enzyme to form a compound of Formula (II).

The reaction may be performed using a suitable oxidative enzyme, for example a mono-oxygenase enzyme, such as a Baeyer-Villiger mono-oxygenase (BVMO) or a cyclohexanone mono-oxygenase (CHMO) enzyme. In one embodiment, the oxidative enzyme is cyclohexanone mono-oxygenase. The reaction is carried out in the presence of oxygen.

An enzyme co-factor may also be used for this reaction, such as nicotinamide adenine dinucleotide (NAD) or nicotinamide adenine dinucleotide phosphate (NADP). In one embodiment, the enzyme co-factor is nicotinamide adenine dinucleotide phosphate.

A co-enzyme can be used for recycling the co-factor such as keto-reductase, which is familiar to those skilled in the art.

The reaction may be performed in a water and a water-miscible organic solvent. Suitable water-miscible organic solvents include isopropyl alcohol or tetrahydrofuran. In one embodiment, the solvent comprises isopropyl alcohol and water.

The reaction may be carried out at a range of temperatures, for example 10° C. to 50° C. In one embodiment, the reaction is carried out between 25° C. and 35° C. The reaction may be carried out at a range of pH, such as from pH 7 to pH 10. In a further embodiment, the reaction is performed at pH 8, using a potassium phosphate buffer, for example potassium biphosphate.

In a further aspect of the disclosure, there is provided a process for preparing a compound of Formula (I) comprising the step of reacting a compound of Formula (XI) with a boron reagent in the presence of a palladium catalyst, followed by the addition of diethanolamine, to form a compound of Formula (XIIb).

In a further aspect of the disclosure, therefore, there is provided a process for preparing a compound of Formula (I) comprising:

(a) cyclopropanating a compound of Formula (IX) followed by hydrolysis to form a compound of Formula (VIII);

(b) reacting an activated form of compound of Formula (VIII) with a malonate derivative then decarboxylating to form a compound of Formula (VII);

(c) reacting a compound of Formula (VII) with urea or thiourea to form a compound of Formula (VI);

(d) reacting a compound of Formula (VI) with a suitable reagent to form a compound of Formula (V);

(e) reacting a compound of Formula (V) with a chlorinating reagent or other activating reagent to form a compound of Formula (IV);

(f) coupling a compound of Formula (IV) with (R)-3-methylmorpholine, or a salt thereof, to form a compound of Formula (III);

(g) reacting a compound of Formula (III) with an oxidising enzyme to form a compound of Formula (II);

(h) reacting a compound of Formula (II) with a nitrogen source followed by iodobenzene diacetate to form a compound of Formula (X), or salt thereof;

(i) reacting a compound of Formula (XI) with a boron reagent in the presence of a palladium catalyst, or lithium-halogen exchange followed by a boron reagent, to form a compound of Formula (XII);

(j) reacting a compound of Formula (X), or salt thereof, with a compound of Formula (XII) to form a compound of Formula (I);

wherein $LG^1$ and $LG^2$ each independently represent chlorine, bromine or triflate.

In one embodiment, $LG^1$ and $LG^2$ both represent chlorine.

In one embodiment, $LG^1$ and $LG^2$ each independently represent bromine or triflate.

In an alternative aspect of the disclosure, there is provided a process for preparing a compound of Formula (I) comprising:

(a) cyclopropanating a compound of Formula (IX) followed by hydrolysis to form a compound of Formula (VIII);

(b) reacting a compound of Formula (VIII) with $R^1$—OH, where $R^1$ is a phthalimide or tetrachlorophthalimide group, to form a compound of Formula (XIII);

(c) reacting a compound of Formula (XIII) with a 2,4-difunctionalised pyrimidine in the presence of light and a photo-catalyst to form a compound of Formula (IV);

(d) coupling a compound of Formula (IV) with (R)-3-methylmorpholine, or a salt thereof, to form a compound of Formula (III);

(e) reacting a compound of Formula (III) with an oxidising enzyme to form a compound of Formula (II);

(f) reacting a compound of Formula (II) with a nitrogen source followed by iodobenzene diacetate to form a compound of Formula (X), or salt thereof;

(g) reacting a compound of Formula (XI) with a boron reagent in the presence of a palladium catalyst or metal-halogen exchange followed by a boron reagent to form a compound of Formula (XII);

(h) reacting a compound of Formula (X), or salt thereof, with a compound of Formula (XII) to form a compound of Formula (I);

wherein $LG^1$ and $LG^2$ represent chlorine, bromine or triflate.

In one embodiment, $LG^1$ and $LG^2$ both represent chlorine.

In one embodiment, $LG^1$ and $LG^2$ represent bromine or triflate.

In one aspect, there is provided a process for preparing a compound of Formula (I) according to Scheme 13:

Scheme 13

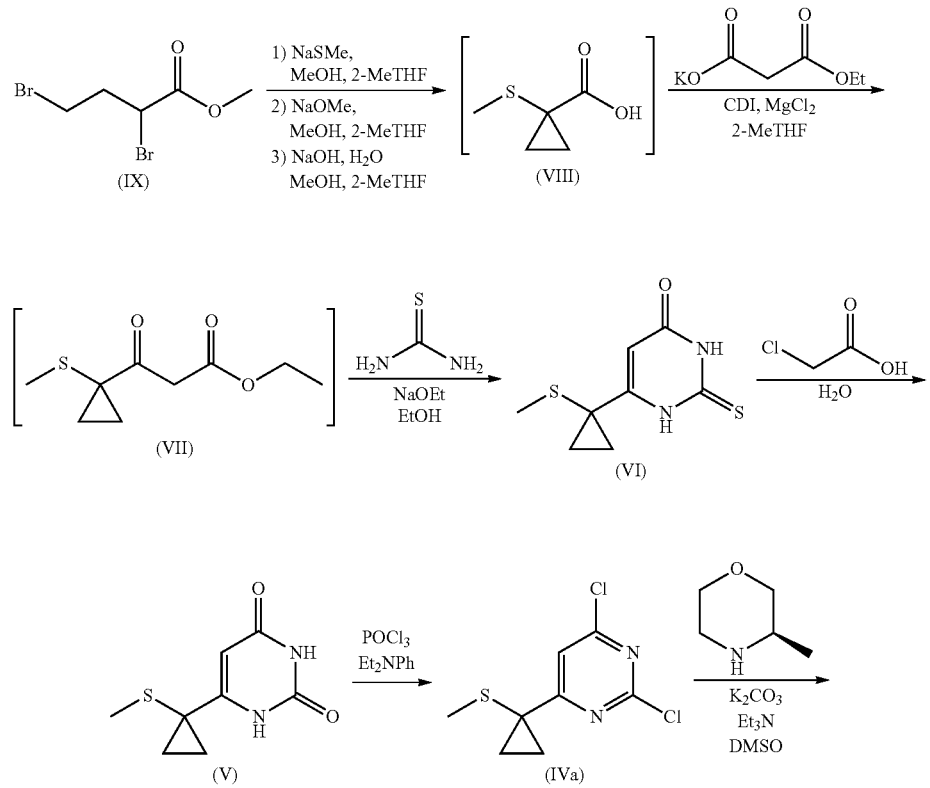

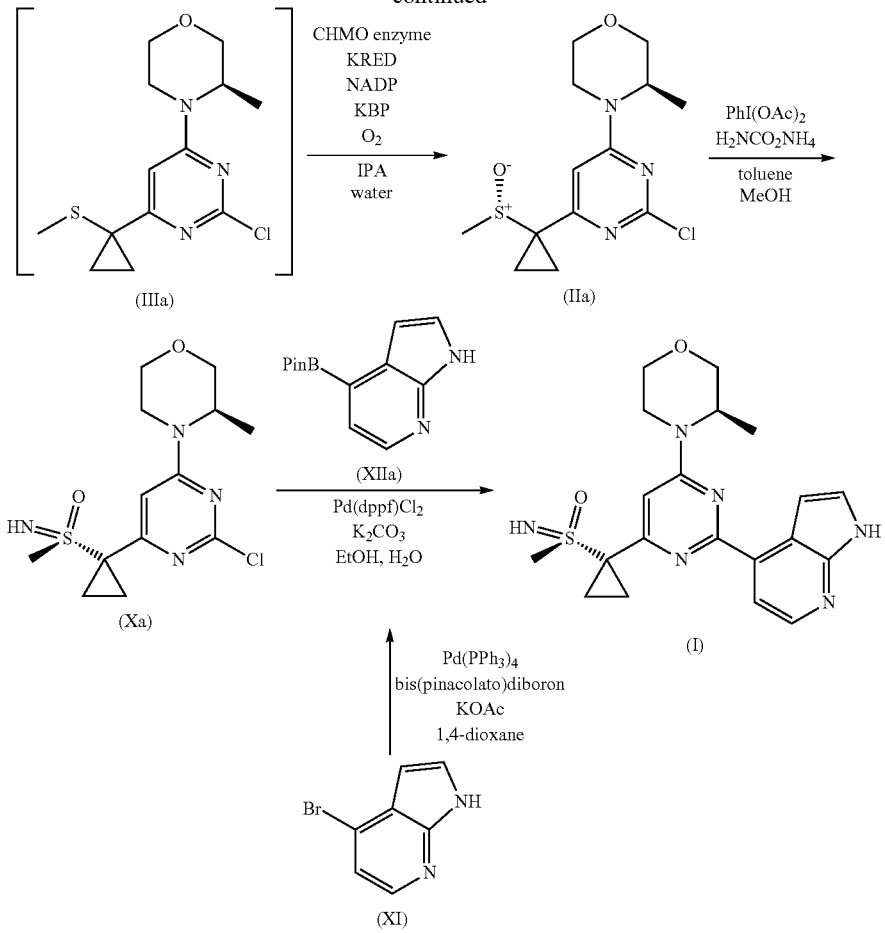
In another aspect, there is provided an alternative process for preparing a compound of Formula (I) according to Scheme 14:
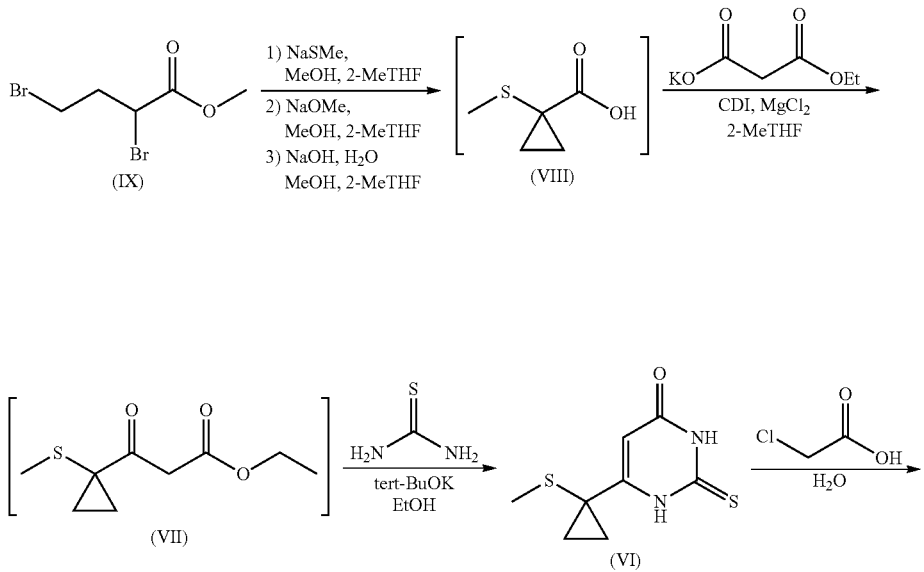

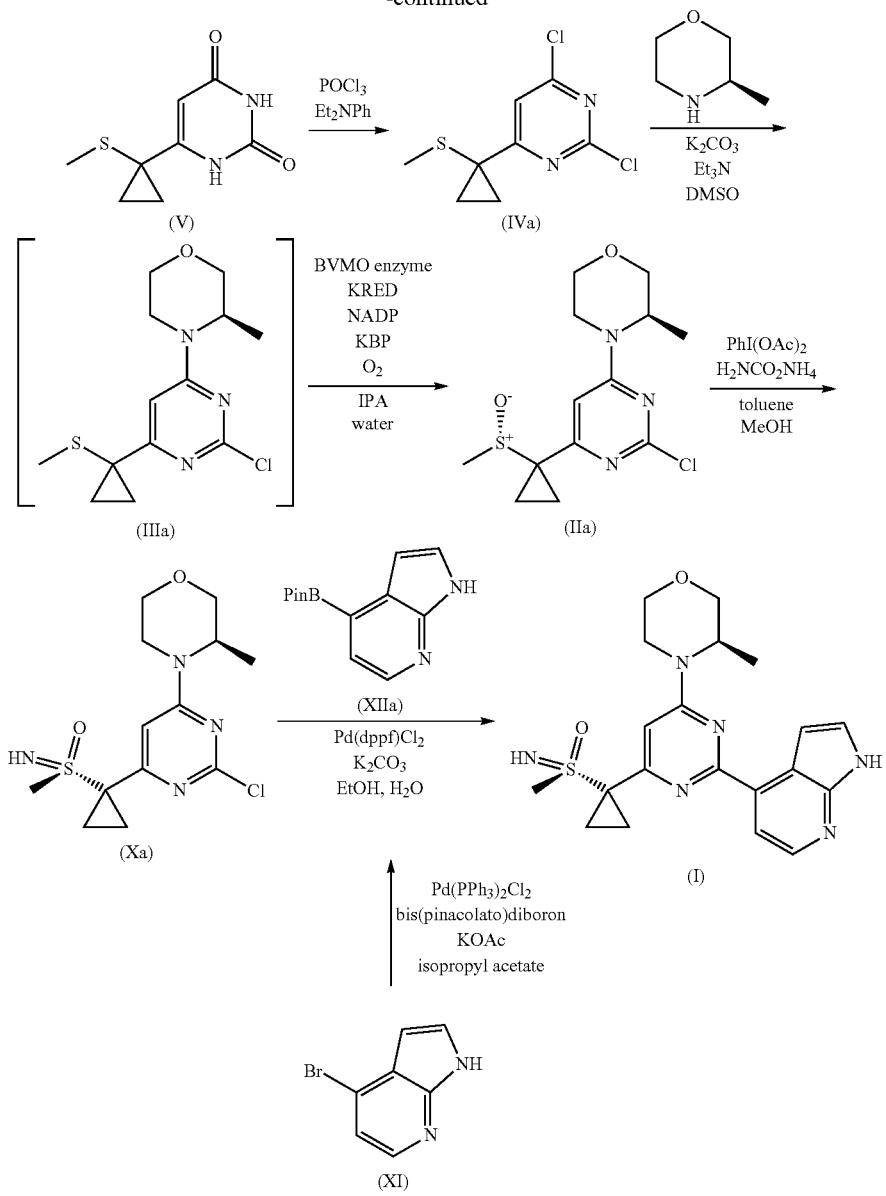
In an alternative aspect, in the step to form the compound of Formula (XIIa) in Schemes 13 and 14, the step further comprises the addition of diethanolamine and therefore the compound of Formula (XIIa) is instead the compound of Formula (XIIb).
In an alternative aspect, there is provided a process for preparing a compound of Formula (I) according to Scheme 15:
Scheme 15
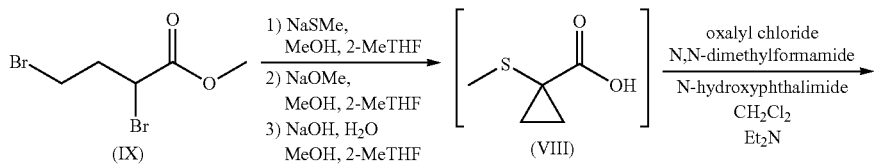

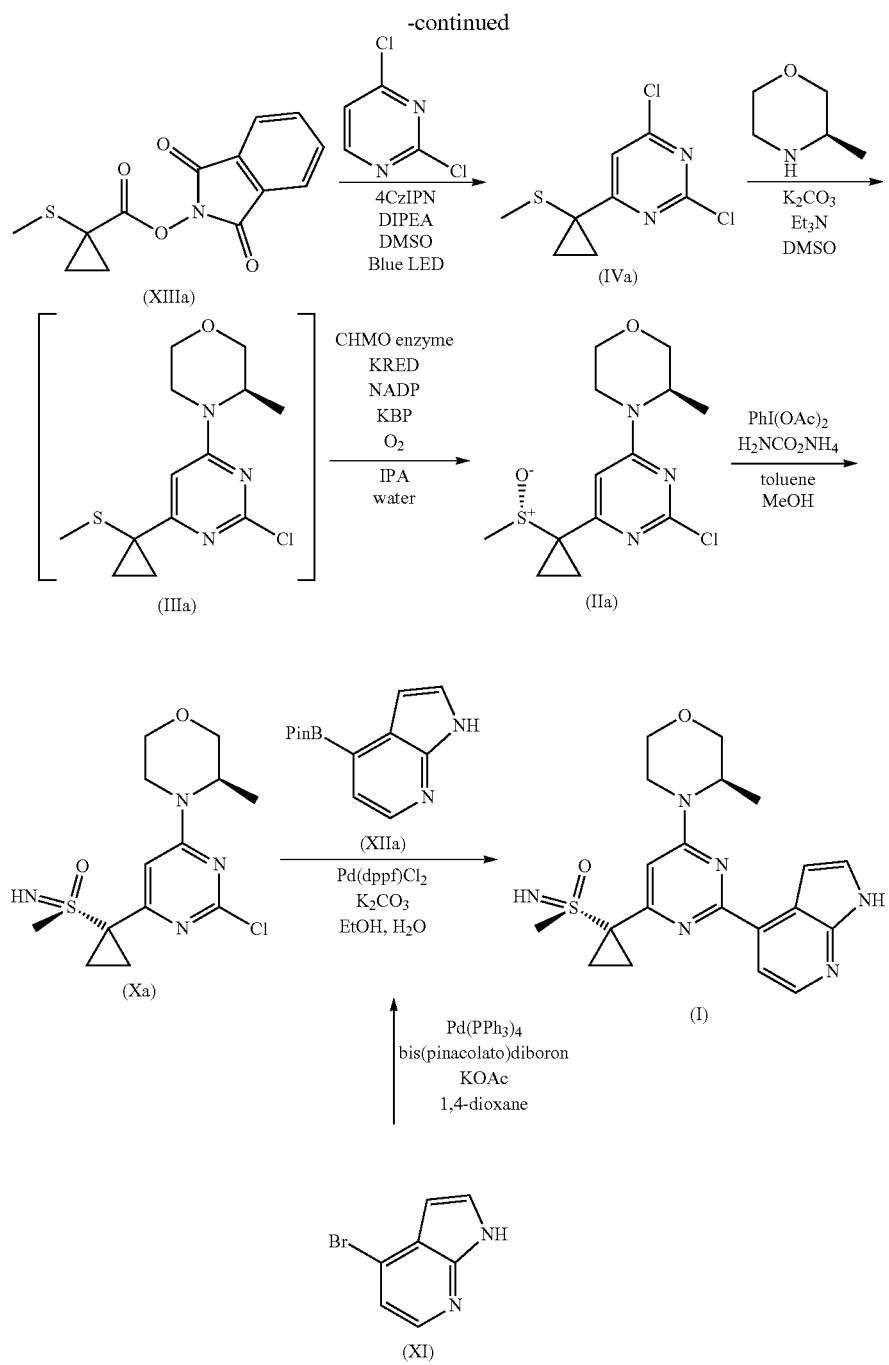
In another aspect, there is provided an alternative process for preparing a compound of Formula (I) according to Scheme 16:
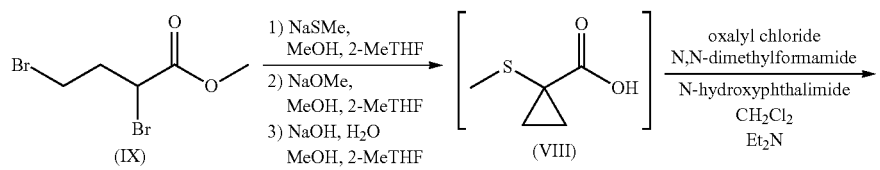

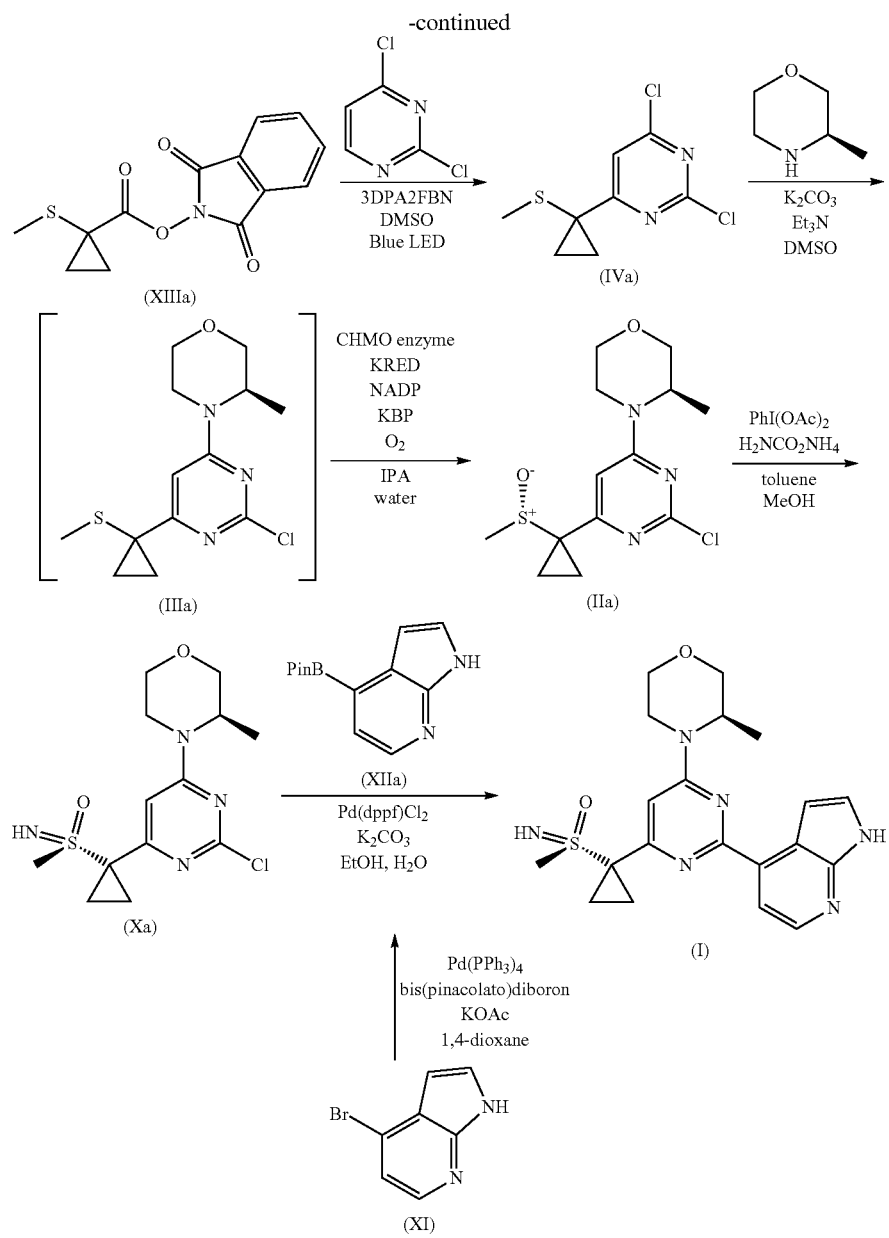

In an alternative aspect, in the step to form the compound of Formula (XIIa) in Scheme 15 or Scheme 16, the step further comprises the addition of diethanolamine and therefore the compound of Formula (XIIa) is instead a compound of Formula (XIIb).

Abbreviations

BPin 4,4,5,5-tetramethyl-1,3,2-dioxaborolane
CDI carbonyldiimidazole
CHMO cyclohexanone monooxygenase
DCM methylene dichloride
DMF dimethylformamide
DMSO dimethyl sulfoxide
DIPEA N,N-diisopropylethylamine
$Et_2N$ triethylamine
$Et_2NPh$ N,N-diethylaniline
EtOH ethanol
IPA isopropyl alcohol
IPrOAc isopropyl acetate
KBP potassium biphosphate
$K_2CO_3$ potassium carbonate
KOAc potassium acetate
KRED keto-reductase
$LiBH_4$ lithium borohydride
mCPBA meta-chloroperoxybenzoic acid
MeOH methanol
2-MeTHF 2-methyltetrahydrofuran
$MgCl_2$ magnesium chloride
MgO magnesium oxide
MsCl methanesulfonyl chloride
NADP nicotinamide adenine dinucleotide phosphate
NaOEt sodium ethoxide
NaOH sodium hydroxide
NaSMe sodium thiomethoxide
NaOMe sodium methoxide Pd(dppf)Cl$_2$ 1,1'-bis(diphenylphosphino)ferrocene
Pd(PPh$_3$)$_4$ tetrakis(triphenylphosphine)palladium(O)
Pd(PPh$_3$)$_2$Cl$_2$ bis(triphenylphosphine)palladium(II) dichloride
Pd(OAc)$_2$ palladium acetate
PhI(OAc)$_2$ phenyliododiacetate
POCl$_3$ phosphoryl chloride
PPh$_3$ triphenylphosphine
Rh(OAc)$_2$ rhodium(II) acetate dimer
tert-BuOK potassium tert-butoxide
THF tetrahydrofuran

GENERAL METHODS

Unless stated otherwise, starting materials were commercially available. All solvents and commercial reagents were of laboratory grade and were used as received. Unless stated otherwise, all operations were carried out at ambient temperature, i.e. in the range 17 to 28° C. and, where appropriate, under an atmosphere of an inert gas such as nitrogen.

Large scale reactions were carried out in stainless steel or glass-lined steel reactors fitted with heat transfer jackets and serviced with appropriate ancillary equipment.

Photo-flow reactions were carried out in a commercial Vapourtec UV-150 ® flow reactor using blue LEDs.

When given, 1H NMR spectra were recorded on a Bruker DRX 500 (500 MHz), a Bruker 400 (400 MHz). Either the central peaks of chloroform-d (CDCl3; δH 7.27 ppm) or dimethylsulfoxide-d6 (d6-DMSO; δH 2.50 ppm), or an internal standard oftetramethylsilane (TMS; δH 0.00 ppm) were used as references. Sample solutions may also contain an internal standard (for example maleic acid or 2,3,5,6-tetrachloronitrobenzene) for assay determination and/or added trifluoroacetic acid, to move exchangeable proton signals (e.g. from maleic acid) away from analyte resonances. Spectral data is reported as a list of chemical shifts (6, in ppm) with a description of each signal, using standard abbreviations (s=singlet, d=doublet, m=multiplet, t=triplet, q=quartet, br=broad, etc.). It is well known in the art that chemical shifts and J-coupling constants may vary slightly as a result of sample preparation differences, for example analyte concentration and whether or not additives (for example NMR assay standards or trifluoroacetic acid) are included.

In general, the compounds were named using the "Structure to Name" part of Biovia Draw 2016.

Example 1: Preparation of 1-(methylsulfanyl)cyclopropanecarboxylic acid

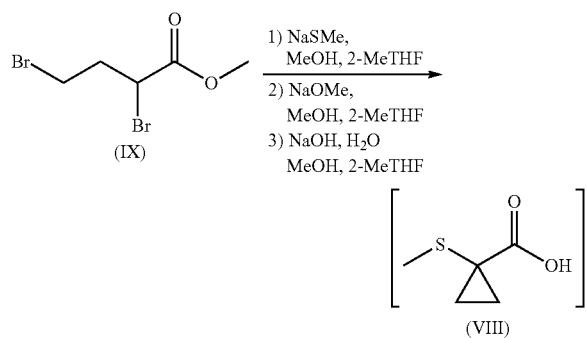

Methyl 2,4-dibromobutyrate (221 kg, 851 mol, 1.0 equiv.) and 2-methyltetrahydrofuran (758 kg) were charged to the vessel at 10-15° C. A solution of sodium thiomethoxide (59.7 kg, 851 mol, 1.0 equiv.) in methanol (184 kg) was charged to the vessel at 10-20° C. The contents of the vessel were stirred at 15-25° C. for 4 hours. A solution of sodium methoxide (53.1 kg, 1.15 equiv.) in methanol (160 kg) was charged to the vessel at 15-25° C. The contents of the vessel were stirred at 15-25° C. for 2 hours. An aqueous solution of sodium hydroxide (2M, 510.6 L, 1.2 equiv.) was charged to the vessel at 15-25° C. The contents of the vessel were stirred at approximately 20° C. for 10 hours. The contents of the vessel were concentrated by reduced pressure distillation to a volume of approximately 5 relative volumes. 2-Methyltetrahydrofuran (1512 kg) was charged to the vessel. The mixture was acidified to pH 1-2 with 4 molar aqueous hydrochloric acid solution. The biphasic mixture was stirred for 1 hour, then the batch was allowed to settle. The aqueous layer was removed. The organic solution was washed with aqueous sodium chloride solution (445 kg) and the aqueous layer was removed. The organic solution was washed with aqueous sodium chloride solution (439 kg) and the aqueous layer was removed. The organic solution was concentrated to approximately 2 relative volumes under reduced pressure distillation. 2-Methyltetrahydrofuran (562 kg) was charged to the vessel. The organic solution was concentrated to approximately 2 relative volumes under reduced pressure distillation. 2-Methyltetrahydrofuran (560 kg) was charged to the vessel. The organic solution was concentrated to approximately 2 relative volumes under reduced pressure distillation. 2-Methyltetrahydrofuran (570 kg) was charged to the vessel. The organic solution is concentrated to approximately 2 relative volumes under reduced pressure distillation to yield 1-(methylsulfanyl)cyclopropanecarboxylic acid as a dry 2-methyltetrahydrofuran solution (883 kg, 10.73% w/w, 84% yield). $^1$H NMR (400 MHz, DMSO) 1.12 (2H, q), 1.43 (211, q), 2.15 (311, s).

Example 2: Preparation of ethyl 3-[1-(methylsulfanyl)cyclopropyl]-3-oxopropanoate

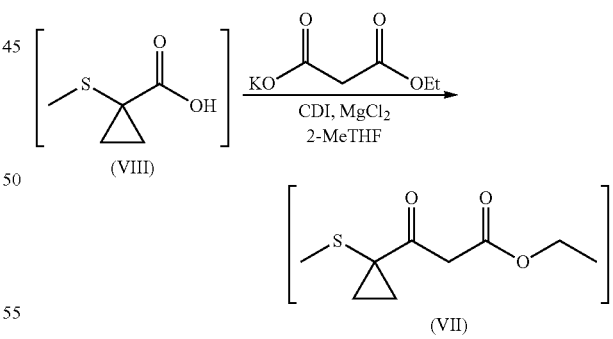

A solution of 1-(methylsulfanyl)cyclopropanecarboxylic acid (94.4 kg, 714.2 mol) in 2-methyltetrahydrofuran (788 kg) was charged to a solution of carbonyldiimidazole (124.4 kg, 752.3 mol) in 2-methyltetrahydrofuran (488 kg) in vessel 1. The contents of vessel 1 were stirred at approximately 20° C. for 4.5 hours. 2-Methyltetrahydrofuran (1206 kg) was charged to vessel 2 then stirring was started. Ethyl potassium malonate (184.1 kg, 1074.4 mol) and magnesium chloride (103 kg, 1074.7 mol) were charged to vessel 2 at 15-25° C. Triethylamine (124.2 kg, 1218 mol) was charged to vessel 2 at 15-25° C. The contents of vessel 2 were stirred at approximately 20° C. for 1 hour. The contents of vessel 1 were transferred to vessel 2 at 15-25° C. The contents of vessel 2 were stirred at approximately 40-45° C. for 15 hours. The mixture was cooled to approximately 20° C. Aqueous hydrochloric acid solution (4M, 1210 kg) was charged to vessel 2. The contents of vessel 2 were stirred for 1 hour then stirring was stopped and the aqueous layer was removed. Water (474 L) was charged to vessel 2. The contents of vessel 2 were stirred for 10 minutes then stirring was stopped and the aqueous layer was removed. Aqueous sodium bicarbonate solution (8% wt/wt, 542 kg) was charged to vessel 2. The contents of vessel 2 were stirred for 1 hour then agitation was stopped and the aqueous layer was removed. Aqueous sodium bicarbonate solution (8% wt/wt, 510 kg) was charged to vessel 2. The contents of vessel 2 were stirred for 1 hour then agitation was stopped and the aqueous layer was removed. A solution of sodium chloride (118 kg) in water (477 kg) was charged to vessel 2. The contents of vessel 2 were stirred for 1 hour then stirring was stopped and the aqueous layer was removed. The organic solution was concentrated to 2-3 relative volumes by reduced pressure distillation. Ethanol (155 kg) was charged to vessel 2. The organic solution was concentrated to 2-3 relative volumes by reduced pressure distillation. Ethanol (153 kg) was charged to vessel 2. The organic solution was concentrated to 3-4 relative volumes by reduced pressure distillation to yield ethyl 3-[1-(methylsulfanyl)cyclopropyl]-3-oxopropanoate as an ethanol solution (473.8 kg, 23.8% w/w, 558 mol, 78% yield). $^1$H NMR (400 MHz, DMSO) 1.19 (3H, t), 1.23-1.32 (2H, m), 1.45-1.60 (2H, m), 2.14 (3H, s), 3.90 (2H, s), 4.10 (2H, q).

Example 3: Preparation of 6-[1-(methylsulfanyl) cyclopropyl]-2-sulfanylidene-2,3-dihydro-4(1H)-pyrimidinone

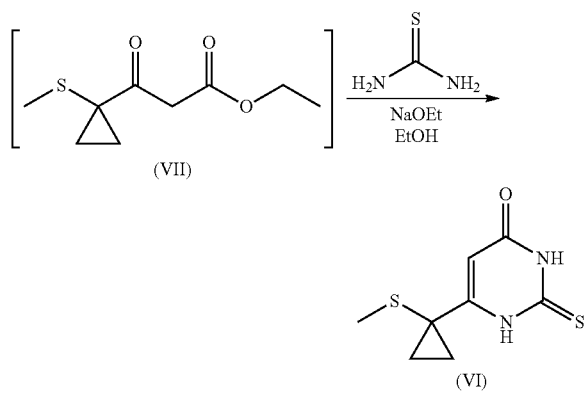

A solution of sodium ethoxide in ethanol (20% w/t, 454.5 kg, 1394 mol) was charged to a stirred solution of thiourea (60.2 kg, 781 mol) in ethanol (90 kg). The contents of the vessel were heated to approximately 78° C. A solution of ethyl 3-[1-(methylsulfanyl)cyclopropyl]-3-oxopropanoate (112.7 kg, 557.7 mol) in ethanol (361 kg) was charged to the vessel. The contents of the vessel were stirred at approximately 78° C. for 15 hours. The contents of the vessel were distilled to a volume of approximately 5 relative volumes under reduced pressure. Aqueous hydrochloric acid solution (2M, 1090 kg) was added slowly at 15-25° C. The contents of the vessel were stirred for 1 hour. The resulting solid was collected by filtration. The filter cake was washed with a mixture of ethanol (178 kg) and 2-methyltetrahydrofuran (48 kg) then dried to yield 6-[1-(methylsulfanyl)cyclopropyl]-2-sulfanylidene-2,3-dihydro-4(1H)-pyrimidinone (77.6 kg, 96.4% w/w, 349.1 mol, 63% yield) as a solid. $^1$H NMR (500 MHz, DMSO, 27° C.) 0.97-1.14 (2H, m), 1.22-1.31 (2H, m), 2.06 (3H, s), 5.72 (1H, s), 12.34 (1H, s), 12.52 (1H, s). MS: (M+H)$^+$ 215.

6-[1-(Methylsulfanyl)cyclopropyl]-2-sulfanylidene-2,3-dihydro-4(1H)-pyrimidinone can also be Prepared as Follows

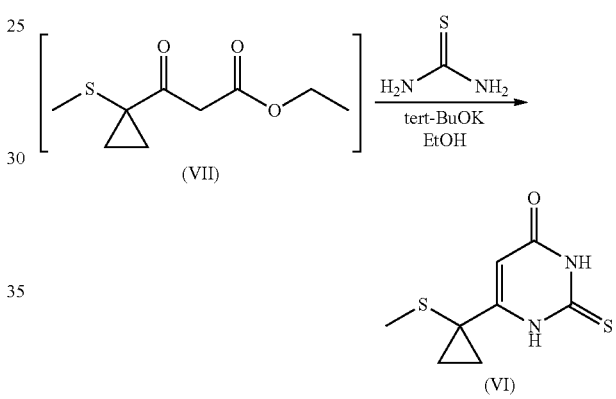

Potassium tert-butoxide (108.6 kg) was charged to tetrahydrofuran (451.2 kg) with stirring. Ethanol (788.2 kg) was added, and the resulting solution was concentrated to approximately 6 relative volumes by reduced pressure distillation. Ethanol (394.1 kg) was charged to the solution, then the resulting solution was concentrated to approximately 6 relative volumes by reduced pressure distillation. Ethanol (394.1 kg) was charged to the solution, then the resulting solution was concentrated to approximately 6 relative volumes by reduced pressure distillation. Thiourea (74.9 kg, 984.0 mol) was charged to the stirred solution, and the resulting mixture was heated to approximately 78° C. A solution of ethyl 3-[1-(methylsulfanyl)cyclopropyl]-3-oxopropanoate (166.5 kg, 824.0 mol) in ethanol (169 kg) was charged to the vessel. The contents of the vessel were stirred at approximately 78° C. for 10 hours. The mixture was cooled to approximately 20° C. then water (666 kg) was charged. Concentrated hydrochloric acid solution (143.2 kg) was added slowly at 15-25° C. The contents of the vessel were stirred for 2 hours. The resulting solid was collected by filtration. The filter cake was washed with a mixture of ethanol (262.7 kg) and water (166.5 kg) then dried to yield 6-[1-(methylsulfanyl)cyclopropyl]-2-sulfanylidene-2,3-dihydro-4(1H)-pyrimidinone (138.4 kg, 95.0% w/w, 614.3 mol, 75% yield) as a solid. $^1$H NMR (500 MHz, DMSO, 27° C.) 0.97-1.14 (2H, m), 1.22-1.31 (2H, m), 2.06 (3H, s), 5.72 (1H, s), 12.34 (1H, s), 12.52 (1H, s). MS: (M+H)$^+$ 215.

Example 4: Preparation of 6-[1-(methylsulfanyl)cyclopropyl]-2,4(1H,3H)-pyrimidinedione

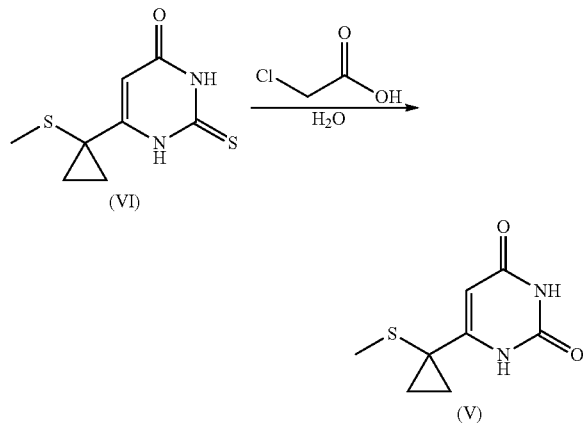

6-[1-(Methylsulfanyl)cyclopropyl]-2-sulfanylidene-2,3-dihydro-4(1H)-pyrimidinone (76.8 kg, 345 mol) and water (607 kg) were charged to the vessel. Agitation was started. Chloroacetic acid (162.5 kg, 1719 mol) was charged to the vessel. The contents of the vessel were stirred at approximately 95° C. for 9 hours then cooled to approximately 5° C. The resulting solid was collected by filtration. The filter cake was washed with aqueous hydrochloric acid solution (4 Molar, 238 kg). The resulting solid was dried at approximately 40° C. to yield 6-[1-(methylsulfanyl)cyclopropyl]-2,4(1H,3H)-pyrimidinedione (52.7 kg, 97.4% w/w, 259 mol, 75% yield) as a solid. $^1$H NMR (400 MHz, DMSO, 27° C.) 0.95-1.13 (2H, m), 1.19-1.32 (2H, m), 2.08 (3H, s), 5.41 (1H, t), 10.94 (2H, s). MS: $(M+H)^+$ 199.

Example 5: Preparation of 2,4-dichloro-6-[1-(methylsulfanyl)cyclopropyl]pyrimidine

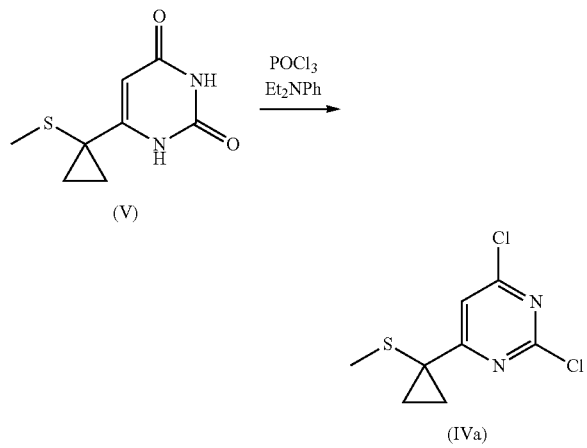

Phosphoryl chloride (335 kg) was charged to vessel 1. Stirring was started. 6-[1-(Methylsulfanyl)cyclopropyl]-2-sulfanylidene-2,3-dihydro-4(1H)-pyrimidinone (52.2 kg, 254 mol) was charged to vessel 1. N,N-diethylaniline (96 kg, 636 mol, 2.5) was charged to vessel 1 at 15-25° C. Water (1.85 kg) was slowly charged to vessel 1, maintaining the temperature below 50° C. The contents of vessel 1 were heated at 90-100° C. for 7 hours. The contents of vessel 1 were cooled to 15-25° C. A solution of sodium acetate (10.1 kg) in water 306 kg) was charged to vessel 2. The contents of vessel 1 and an aqueous solution of sodium hydroxide (25% w/w, 1157 kg) were added to vessel 2 simultaneously, keeping the internal temperature in the range 15-30° C., and the pH in the range 5-8. The resulting mixture was stirred at 0-10° C. for a further 2 hours. A solution of hydrochloric acid (4M) was added to adjust the pH to pH 4. The solid was collected by filtration. The filter cake was washed with water (407 kg) then dried at 30-40° C. to yield 2,4-dichloro-6-[1-(methylsulfanyl)cyclopropyl]pyrimidine (51.4 kg, 92% w/w, 201 mol, 79% yield) as a solid. $^1$H NMR (500 MHz, DMSO, 27° C.) 1.42-1.55 (2H, m), 1.61-1.77 (2H, m), 2.14 (3H, s), 8.03 (1H, s). MS: $(M+H)^+$ 235.

Example 6: Preparation of (3R)-4-{2-chloro-6-[1-(methylsulfanyl)cyclopropyl]-4-pyrimidinyl}-3-methylmorpholine

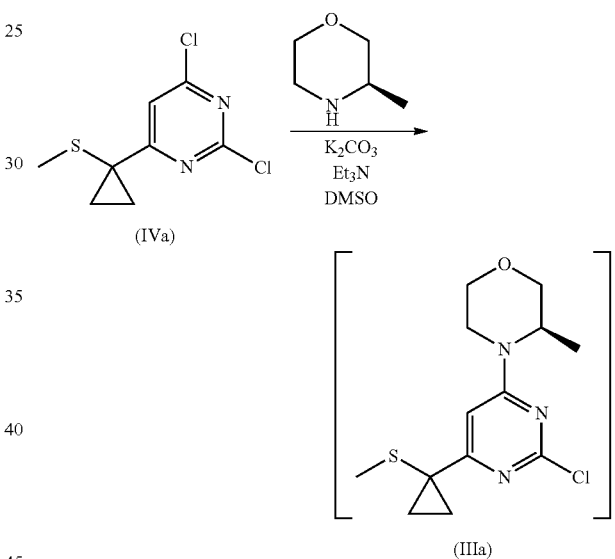

Dimethylsulfoxide (261 kg) was charged to vessel 1. Stirring was started. 2,4-Dichloro-6-[1-(methylsulfanyl)cyclopropyl]pyrimidine (51.0 kg, 200 mol) was charged to vessel 1. Potassium carbonate (72.5 kg) was charged to vessel 1. (R)-3-Methylmorpholine hydrochloride (33.9 kg, 230 mol) was charged to vessel 1. Triethylamine (52.5 kg) was charged to vessel 1. The contents of vessel 1 were stirred at approximately 20° C. for 15 hours. Heptane (324 kg) and water (335 kg) were charged to vessel 1. The contents of vessel 1 were stirred for 30 minutes then a small amount of solid material was removed by filtration and the layers were separated. The organic layer was charged to vessel 2 and washed with water (189 kg). The aqueous layer was removed. Aqueous hydrochloric acid solution (4M, 940 kg) was charged to vessel 2. The contents of vessel 2 were agitated for 30 minutes, then the layers were allowed to settle. The aqueous layer was removed and transferred to vessel 3. Aqueous hydrochloric acid solution (4M, 141 L) was charged to vessel 2. The contents of vessel 2 were agitated for 30 minutes, then the layers were allowed to settle. The aqueous layer was removed and transferred to vessel 3. tert-Butyl methyl ether (350 kg) was charged to the stirred contents of vessel 3. Aqueous NaOH solution (50% w/w, 353 kg) was slowly charged to vessel 3 until the contents were adjusted to pH 14. Stirring was stopped and the layers were allowed to settle. The layers were separated then the aqueous layer was re-charged to vessel 3. Tert-Butyl methyl ether (104 kg) was charged to vessel 3. The mixture was stirred for 20 minutes, then agitation was stopped and the layers were allowed to settle. The aqueous layer was removed, then both tert-butyl methyl ether solutions were combined in vessel 3. The contents of vessel 3 were concentrated by reduced pressure distillation to a volume of approximately 3 relative volumes. Isopropyl alcohol (150 kg) was charged to vessel 3 then the contents of vessel 3 were concentrated by distillation to a volume of approximately 3 relative volumes. Isopropyl alcohol (150 kg) was charged to vessel 3 then the contents of vessel 3 were concentrated by distillation to a volume of approximately 3 relative volumes. The solid was collected by filtration to yield (3R)-4-{2-chloro-6-[1-(methylsulfanyl)cyclopropyl]-4-pyrimidinyl}-3-methylmorpholine (27.6 kg, 96.7% w/w, 89.1 mol, 44% yield) as a solid, and (3R)-4-{2-chloro-6-[1-(methylsulfanyl)cyclopropyl]-4-pyrimidinyl}-3-methylmorpholine as an isopropyl alcohol solution (106 kg, 11.13% w/w, 39.6 mol, 20% yield). Combined yield 64%. $^1$H NMR (500 MHz, DMSO, 27° C.) 1.21 (3H, d), 1.28 (2H, d), 1.44-1.64 (2H, m), 2.12 (3H, s), 3.20 (1H, td), 3.45 (1H, td), 3.59 (1H, dd), 3.72 (1H, d), 3.86-4.12 (2H, m), 4.36 (1H, s), 7.10 (1H, s). MS (M+H)$^+$ 300.

Example 7: Preparation of (3R)-4-(2-chloro-6-{1-[(R)-methylsulfinyl]cyclopropyl}-4-pyrimidinyl)-3-methylmorpholine

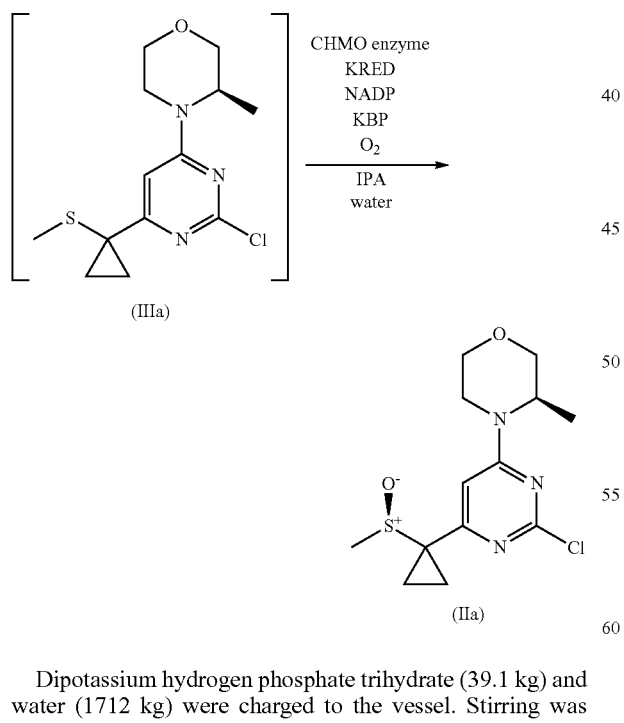

Dipotassium hydrogen phosphate trihydrate (39.1 kg) and water (1712 kg) were charged to the vessel. Stirring was started then concentrated hydrochloric acid (2.1 kg) was added. A solution of (3R)-4-{2-chloro-6-[1-(methylsulfanyl) cyclopropyl]-4-pyrimidinyl}-3-methylmorpholine (35.36 kg, 117.9 mol) in isopropyl alcohol (109 kg) was charged to the vessel. Nicotinamide adenine dinucleotide phosphate (0.68 kg) was charged to the vessel. Cyclohexanone monooxygenase *Rhodococcus Ruber* (accession number AAL14233.1, crude cell lysate, 277.3 kg, 8% w/w) was charged to the vessel. Keto-reductase (Asymchem 6511, 69.5 kg) was charged to the vessel. A mixture of air and nitrogen (1:2) was blown through the reaction mixture using a sparger, and the contents of the vessel were stirred at approximately 30° C. for 10 hours. The contents of the vessel were adjusting to pH 3 using 10% aqueous hydrochloric acid solution (40.6 kg). Sodium chloride (520 kg) was charged to the vessel. The resulting mixture was stirred for 2 hours. The solid was removed by centrifugation, and the filter cake was washed with ethyl acetate (3×310 kg). The combined filtrate was charged to a clean vessel, then water (505 kg) was added. The mixture was stirred for 1 hour, then the aqueous layer was removed. The organic layer was concentrated to a total volume of 1000 L by reduced pressure distillation. The mixture was filtered. A solution of sodium hydroxide (68.7 kg) in water (276.3 kg) was added at 15-30° C. The resulting mixture was extracted with ethyl acetate (3×636 kg). The combined organic phases were washed with water (689 kg). The resulting organic solution was concentrated by reduced pressure distillation to a total volume of approximately 150 L. Heptane (235 kg) was charged to the vessel, then the contents of the vessel were concentrated by reduced pressure distillation to a total volume of approximately 150 L. Heptane (235 kg) was charged to the vessel, then the contents of the vessel were concentrated by reduced pressure distillation to a total volume of approximately 150 L. The contents of the vessel were stirred at 80° C. for 2 hours then cooled to approximately 10° C. and stirred for a further 4 hours. The solid was collected by filtration. The filter cake was washed with heptane (185 kg) and dried to yield (3R)-4-(2-chloro-6-{1-[(R)-methylsulfinyl]cyclopropyl}-4-pyrimidinyl)-3-methylmorpholine (28.5 kg, 95.2% w/w, 86.07 mol, 73% yield) as a solid. $^1$H NMR (400 MHz, DMSO, 27° C.) 1.20 (3H, d), 1.26-1.34 (2H, m), 1.40-1.52 (2H, m), 2.52 (3H, s), 3.17 (1H, td), 3.42 (1H, td), 3.57 (1H, dd), 3.71 (1H, d), 3.92 (1H, dd), 4.01 (1H, d), 4.36-4.40 (1H, m), 6.66 (1H, s). MS: (M+H)$^+$ 316.

Example 8: Preparation of (3R)-4-{2-chloro-6-[1-(S-methylsulfonimidoyl)cyclopropyl]-4-pyrimidinyl}-3-methylmornholine hydrochloride

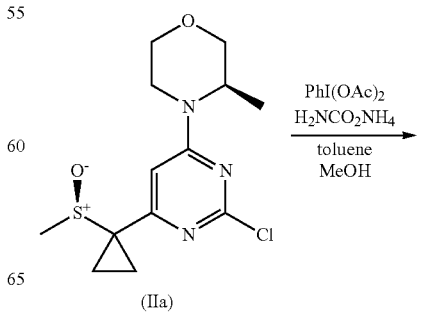

-continued

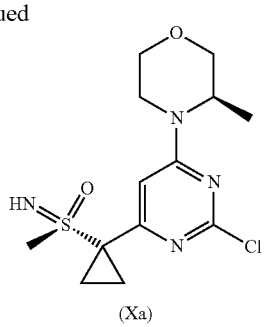

(Xa)

Toluene (258 kg) and methanol (47.4 kg) were charged to the vessel. Stirring was started, and the contents were cooled to 0-10° C. (3R)-4-(2-Chloro-6-{1-[(R)-methylsulfinyl]cyclopropyl}-4-pyrimidinyl)-3-methylmorpholine (31.7 kg, 94.26 mol) and (diacetoxyiodo)benzene (65.0 kg, 197.9 mol) were charged to the vessel at 0-10° C. Ammonium carbamate (30 kg, 377.0 mol) was charged to the vessel at 0-10° C., then the contents of the vessel were stirred at 0-10° C. for 20 hours. Aqueous citric acid solution (30% w/w) was charged to the vessel until the pH was adjusted to pH 2-3. The mixture was stirred for 30 minutes. Stirring was stopped and the aqueous layer was removed. Stirring was re-started, then aqueous citric acid solution (30% w/w) was charged to the vessel until the pH was adjusted to pH 2. Stirring was stopped and the layers were partitioned. The aqueous phases were combined and stirring was started. Aqueous sodium hydroxide solution (30% w/w) was charged until the pH was adjusted to pH 8-9. Sodium chloride (96 kg) was charged. Ethyl acetate (101 kg) and tetrahydrofuran (33 kg) were charged, and the resulting mixture was stirred for 30 minutes. Stirring was stopped and the layers were partitioned. The aqueous layer was re-charged to the vessel and stirring was started. Ethyl acetate (89.1 L) and tetrahydrofuran (29.7 L) were charged, and the resulting mixture was stirred for 30 minutes. Stirring was stopped and the layers were partitioned. The aqueous layer was re-charged to the vessel and stirring was started. Ethyl acetate (101 kg) and tetrahydrofuran (33 kg L) were charged, and the resulting mixture was stirred for 30 minutes. Stirring was stopped and the layers were partitioned. The aqueous layer was re-charged to the vessel and stirring was started. Ethyl acetate (101 kg) and tetrahydrofuran (33 kg L) were charged, and the resulting mixture was stirred for 30 minutes. Stirring was stopped and the layers were partitioned. The organic phases were combined in the vessel then concentrated to approximately 59 L by distillation. Isopropyl alcohol (48 kg) was charged, then the solution was concentrated to approximately 59 L by distillation. Isopropyl alcohol (48 kg) was charged, then the solution was concentrated to approximately 59 L by distillation. The resulting solution was cooled to 0-5° C., then a solution of hydrogen chloride in isopropyl alcohol (6M, 21.7 kg) was charged to the vessel. The resulting mixture was stirred at 0-5° C. for approximately 2 hours. Methyl tert-butyl ether (135 kg) was charged to the vessel, and the contents were stirred for a further 2 hours. The solid was collected by filtration and washed with methyl tert-butyl ether (45 kg). The solid was re-charged to the vessel, then methanol (54 kg) was added. The slurry was stirred at 35-40° C. for 1 hour then cooled to 20-25° C. Methyl tert-butyl ether (103 kg) was charged to the vessel and the mixture was stirred for 1 hour. The solid was collected by filtration, then the filter cake was washed with methyl tert-butyl ether (59 L) and dried to yield (3R)-4-{2-chloro-6-[1-(S-methylsulfonimidoyl)cyclopropyl]-4-pyrimidinyl}-3-methylmorpholine hydrochloride (30.2 kg, 78.2 mol, 83% yield) as a solid. $^1$H NMR (500 MHz, DMSO, 27° C.) 1.23 (3H, d), 1.65-1.70 (1H, m), 1.85-1.89 (3H, m), 3.18-3.24 (1H, m), 3.42 (1H, td), 3.58 (1H, dd), 3.73 (3H, s), 3.80-3.87 (1H, m), 3.95 (1H, dd), 4.05-4.15 (1H, m), 4.34-4.46 (1H, m), 7.12 (1H, s). MS: (M+H)$^+$ 331.

Example 9: Preparation of 4-(4,4,5,5-tetramethyl-1,3,2-dioxaborolan-2-yl)-1H-pyrrolo[2,3-b]pyridine

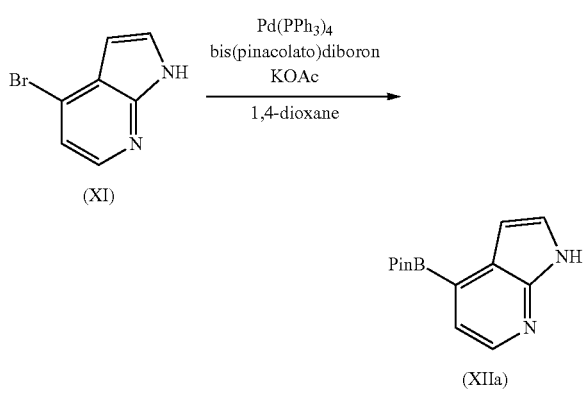

1,4-Dioxane (938 kg) was charged to the vessel. The vessel was inerted with nitrogen and stirring was started. 4-Bromo-7-azaindole (62.6 kg, 304.5 mol) was charged to the vessel. Potassium acetate (62.3 kg, 615 mol) was charged to the vessel. Bis(pinacolato)diboron (105.5 kg, 397.2 mol) was charged to the vessel. Tetrakis(triphenylphosphine)palladium(0) (3.67 kg, 3.05 mol) was charged to the vessel. The contents of the vessel were heated at 90-100° C. for 12 hours. The mixture was cooled to 25-35° C. and the solid was removed by filtration. The filter cake was washed with 1,4-dioxane (105 kg) then the combined filtrate was charged to a vessel. The filtrate was concentrated to a volume of approximately 125 L by reduced pressure distillation. The contents of the vessel were heated to 40° C., then water (189 kg) was charged to the vessel. The contents of the vessel were stirred at approximately 20° C. for 12 hours, then the solid was collected by filtration. The filter cake was washed with water (2×63 kg). The solid and methyl tert-butyl ether (237 kg) were charged to a vessel, and the mixture was stirred at approximately 35° C. for 30 minutes. The mixture was cooled to approximately 15° C. and stirred for a further 4 hours. The solid was collected by filtration. The filter cake was washed with methyl tert-butyl ether (46 kg) then dried at approximately 40° C. to yield 4-(4,4,5,5-tetramethyl-1,3,2-dioxaborolan-2-yl)-1H-pyrrolo[2,3-b]pyridine (57.5 kg, 96% w/w, 222.3 mol, 73% yield) as a solid. $^1$H NMR (500 MHz, DMSO) 1.35 (12H, s), 6.67 (1H, dd), 7.30 (1H, d), 7.44-7.57 (1H, m), 8.23 (1H, d), 11.65 (1H, s).

4-(4,4,5,5-Tetramethyl-1,3,2-dioxaborolan-2-yl)-1H-pyrrolo[2,3-b]pyridine can Also be Prepared as Follows

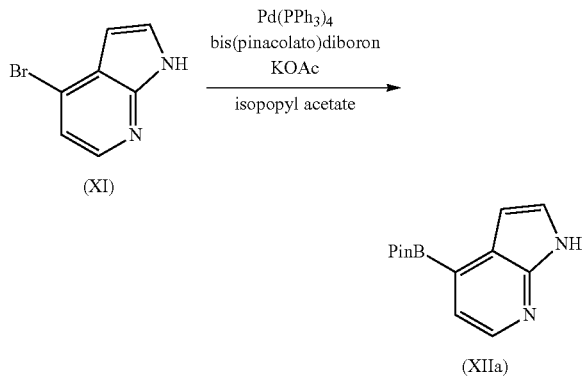

Isopropyl acetate (387 kg) was charged to the vessel. The vessel was inerted with nitrogen and stirring was started. 4-Bromo-7-azaindole (41.5 kg, 211 mol) was charged to the vessel. Potassium acetate (43.1 kg, 439 mol) was charged to the vessel. Bis(pinacolato)diboron (54.7 kg, 215.4 mol) was charged to the vessel. Bis(triphenylphosphine)palladium(II) dichloride (2.9 kg, 4.13 mol) was charged to the vessel. The contents of the vessel were heated at 85-90° C. for 22 hours. The mixture was cooled to 50° C. then washed with water (4×218 kg). Mercapto silica (27.8 kg) was added to the organic phase and the mixture was heated at 50° C. for 8 hours. The solid was removed by filtration and the filter cake was washed with isopropyl acetate (98 kg). The combined filtrate was concentrated by reduced pressure distillation to a volume of approximately 240 L. The mixture was cooled to approximately 27° C. then methyl tert-butyl ether (200 kg) was added. The mixture was cooled to approximately 3° C. and stirred for a further 7 hours. The solid was collected by filtration. The filter cake was washed with methyl tert-butyl ether (40 kg) then dried at approximately 40° C. to yield 4-(4,4,5,5-tetramethyl-1,3,2-dioxaborolan-2-yl)-1H-pyrrolo[2,3-b]pyridine (39.7 kg, 98.9% w/w, 161.0 mol, 76% yield) as a solid. $^1$H NMR (500 MHz, DMSO) 1.35 (12H, s), 6.67 (1H, dd), 7.30 (1H, d), 7.44-7.57 (1H, m), 8.23 (1H, d), 11.65 (1H, s).

Example 9a: Preparation of 4-(1,3,6,2-dioxazaborocan-2-yl)-1H-pyrrolo[2,3-b]pyridine from 4-(4,4,5,5-tetramethyl-1,3,2-dioxaborolan-2-yl)-1H-pyrrolo[2,3-b]pyridine

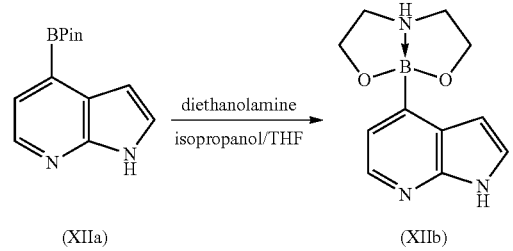

A solution of diethanolamine (1.420 g, 13.51 mmol) in isopropanol (1.4 mL) and tetrahydrofuran (1.4 mL) was added to a solution of 4-(4,4,5,5-tetramethyl-1,3,2-dioxaborolan-2-yl)-1H-pyrrolo[2,3-b]pyridine (3.354 g, 13.47 mmol) in tetrahydrofuran (13.5 mL) with stirring. After 20 minutes, the solid was collected by filtration. The solid was washed twice with a mixture of isopropanol (0.7 mL) and tetrahydrofuran (6.8 mL), then dried in a vacuum oven at 40° C. for 21 hours to yield 4-(1,3,6,2-dioxazaborocan-2-yl)-1H-pyrrolo[2,3-b]pyridine (2.494 g, 77%) as a solid. $^1$H NMR (400 MHz, DMSO, 27° C.) 2.89 (2H, ddt), 3.15 (2H, ddt), 3.83-3.99 (4H, m), 6.56 (1H, dd), 6.97-7.04 (1H, m), 7.08 (1H, d), 7.22-7.26 (1H, m), 8.02 (1H, d), 11.11 (1H, s). MS: (M+H)$^+$ 232.

Example 9b: Preparation of 4-(1,3,6,2-dioxazaborocan-2-yl)-1H-pyrrolo[2,3-b]pyridine from 4-Bromo-7-azaindole

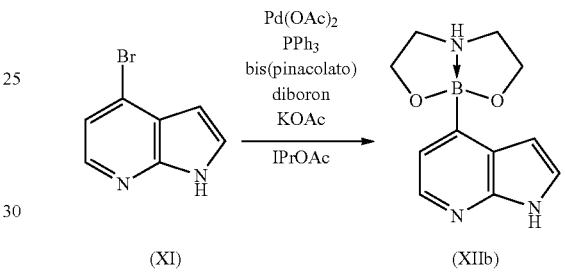

A mixture of 4-bromo-1H-pyrrolo[2,3-b]pyridine (8.00 g, 40.0 mmol), potassium acetate (7.91 g, 80.6 mmol), bis(pinacolato)diboron (13.25 g, 52.18 mmol), palladium acetate (182 mg, 0.811 mmol) and triphenylphosphine (421 mg, 1.61 mmol) in isopropyl acetate (80 mL) was stirred at 90° C. for 21 hours. The mixture was washed with aqueous brine solution (80 mL). The organic layer was diluted with isopropyl acetate (80 mL) and washed with aqueous brine solution (80 mL). The organic layer was concentrated by distillation to a volume of approximately 40 mL. Isopropyl acetate (60 mL) was added to the residual solution, then the organic later was concentrated by distillation to a volume of approximately 40 mL. Isopropyl acetate (60 mL) was added to the residual solution, then the organic layer was concentrated by distillation to a volume of approximately 40 mL. The stirred solution was seeded with 4-(1,3,6,2-dioxazaborocan-2-yl)-1H-pyrrolo[2,3-b]pyridine (0.08 g), obtained, for example, from Example 9a above. A solution of diethanolamine (8.48 g, 80.7 mmol) in isopropanol (30 mL, 186 mmol) was added dropwise at 75° C. The mixture was stirred at 75° C. for a further 13 hours. The solid was collected by filtration. The solid slurry was washed twice with a mixture of isopropanol (2 mL) and 2-methyltetrahydrofuran (20 mL), then dried in a vacuum oven at 40° C. for 21 hours to yield 4-(1,3,6,2-dioxazaborocan-2-yl)-1H-pyrrolo[2,3-b]pyridine (6.653 g, 69%) as a solid. $^1$H NMR (400 MHz, DMSO, 27° C.) 2.89 (2H, ddt), 3.15 (2H, ddt), 3.83-3.99 (4H, m), 6.56 (1H, dd), 6.97-7.04 (1H, m), 7.08 (1H, d), 7.22-7.26 (1H, m), 8.02 (1H, d), 11.11 (1H, s). MS: (M+H)$^+$ 232.

Example 10: Preparation of 4-{4-[(3R)-3-methyl-4-morpholinyl]-6-[1-(S-methylsulfonimidoyl)cyclopropyl]-2-pyrimidinyl}-1H-pyrrolo[2,3-b]pyridine

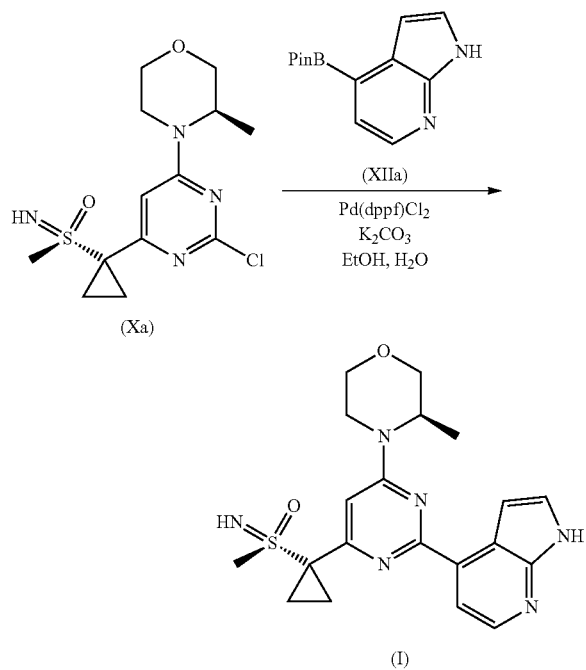

Anhydrous ethanol (376 kg) was charged to the vessel. (3R)-4-{2-Chloro-6-[1-(S-methylsulfonimidoyl)cyclopropyl]-4-pyrimidinyl}-3-methylmorpholine hydrochloride (28.5 kg, 77.68 mol) was charged to the vessel. Stirring was started. A solution of anhydrous potassium carbonate (35.1 kg, 256 mol) in water (136 kg) was charged to the vessel. The vessel was inerted with nitrogen. 4-(4,4,5,5-Tetramethyl-1,3,2-dioxaborolan-2-yl)-1H-pyrrolo[2,3-b]pyridine (25.4 kg, 101.0 mol) was charged to the vessel. [1,1'-Bis(diphenylphosphino)ferrocene]dichloropalladium(II) (1.250 kg, 1.709 mol) was charged to the vessel. The contents of the vessel were heated to approximately 80° C. for 4 hours. The contents of the vessel were cooled to approximately 25° C. then a mixture of activated carbon (1.8 kg) and water (24.8 kg) was charged to the vessel. The contents of the vessel were stirred for 4 hours, then the solid was removed by filtration and the filter cake was washed with ethanol (39 kg). The filtrate was transferred to a clean vessel. The contents of the vessel were concentrated by reduced pressure distillation to a total volume of approximately 100 L. Ethyl acetate (86 kg) was charged to the vessel and the contents were stirred for 1 hour at approximately 25° C., then stirring was stopped and the layers were partitioned. The aqueous layer was re-charged to the vessel. Ethyl acetate (86 kg) was charged to the vessel and the contents were stirred for 30 minutes at approximately 25° C., then stirring was stopped and the layers were partitioned. The organic layers were combined in the vessel. Water (32 kg) was charged to the vessel and the contents were stirred for 30 minutes at approximately 25° C., then stirring was stopped and the aqueous layer was removed. Silica thiol (24.2 kg) was charged to the vessel. The contents of the vessel were stirred at approximately 25° C. for 8 hours. The solid was removed by filtration and the filter cake was washed with ethyl acetate (25 kg). The filtrate was transferred to a clean vessel. The contents of the vessel were concentrated by reduced pressure distillation to a total volume of approximately 65 L. 1-Butanol (40 kg) was charged to the vessel, then the contents of the vessel were concentrated by reduced pressure distillation to a total volume of approximately 65 L. Butanol (40 L) was charged to the vessel, then the contents of the vessel were concentrated by reduced pressure distillation to a total volume of approximately 65 L. The stirred contents of the vessel were heated to approximately 75° C., then seed crystal (17 g) was charged to the vessel. The mixture was stirred for 3 approximately 2 hours, then the mixture was cooled to approximately 20° C. n-Heptane (76 kg) was charged to the vessel and the mixture was stirred at approximately 20° C. for a further 2 hours. The solid was collected by filtration. The filter cake was washed with a mixture of 1-butanol (5 kg) and n-heptane (23 kg) to yield 4-{4-[(3R)-3-methyl-4-morpholinyl]-6-[1-(S-methylsulfonimidoyl)cyclopropyl]-2-pyrimidinyl}-1H-pyrrolo[2,3-b]pyridine (25.5 kg, 97% w/w, 60.0 mol, 77% yield) as a solid. 1H NMR (500 MHz, DMSO, 27° C.) 1.29 (3H, d), 1.42-1.49 (1H, m), 1.55 (2H, ddt), 1.78 (1H, dq), 3.14 (3H, s), 3.29 (1H, td), 3.53 (1H, td), 3.68 (1H, dd), 3.81 (1H, d), 3.88 (1H, s), 4.02 (1H, dd), 4.20 (1H, d), 4.60 (1H, s), 7.02 (1H, s), 7.26 (1H, dd), 7.59-7.65 (1H, m), 7.98 (1H, d), 8.36 (1H, d), 11.83 (1H, s). MS: (M+H)$^+$ 413. Examples 11 and 12 describe an alternative process for the synthesis of 2,4-dichloro-6-[1-(methylsulfanyl)cyclopropyl]pyrimidine from 1-(methylsulfanyl)cyclopropanecarboxylic acid via a photoredox reaction.

Example 11: Preparation of (1,3-dioxoisoindolin-2-yl)1-methylsulfanylcyclopropanecarboxylate

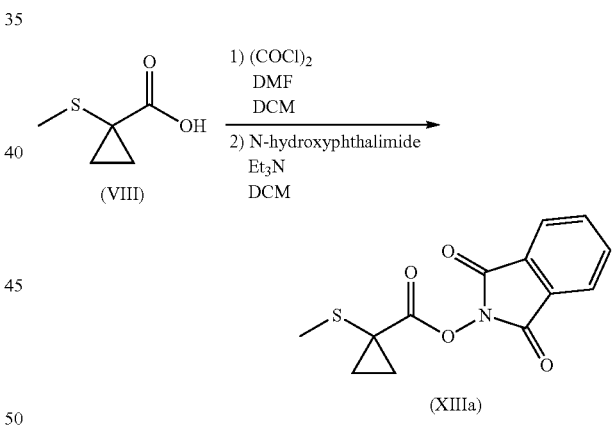

Oxalyl chloride (7.56 g, 59.0 mmol)) was added to a stirred solution of 1-(methylsulfanyl)cyclopropanecarboxylic acid (7.08 g, 53.6 mmol) in dichloromethane (142 mL) at approximately 20° C. Dimethylformamide (0.196 g, 2.68 mmol) was added to the solution. The resulting solution was warmed to 25° C. then stirred for a further 2 hours. The solution was concentrated then re-dissolved in DCM (142 mL). The resulting solution was cooled to approximately 5° C., then N-hydroxyphthalimide (9.92 g, 59.0 mol) was slowly added with stirring. Triethylamine (6.03 g, 59.0 mmol) was added, then the resulting mixture was warmed to approximately 20° C. and stirred for 22 hours. Water (142 mL was charged) to the mixture, then the layers were partitioned. The organic layer was concentrated, then the residue was dissolved in ethyl acetate (53 mL). The solution was warmed to approximately 45° C. with stirring. Heptane (71 mL) was added to the stirred solution, then the mixture was slowly cooled to 20° C. The resulting solid was isolated by filtration, and the filter cake was washed with heptane (21 mL) to yield (1,3-dioxoisoindolin-2-yl)1-methylsulfanylcyclopropanecarboxylate (8.15 g, 99% w/w, 29.2 mmol, 55% yield). 1H NMR (500 MHz, DMSO, 27° C.) 1.46-1.65 (2H, m), 1.67-1.86 (2H, m), 2.32 (3H, s), 7.87-8.06 (4H, m). MS: (M+H)+ 278.

Example 12: Preparation of 2,4-dichloro-6-[1-(methylsulfanyl)cyclopropyl]pyrimidine Via Photoredox

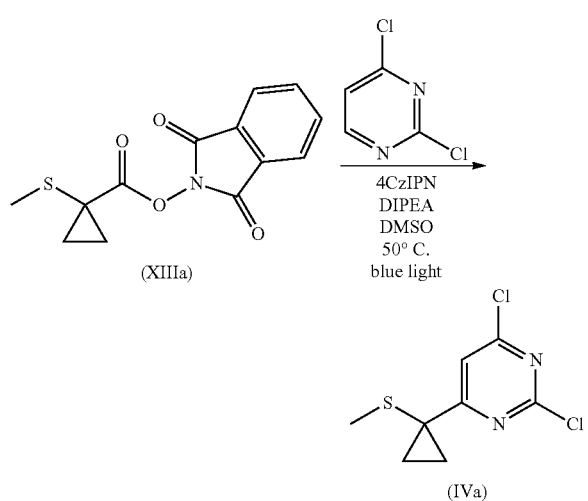

(1,3-Dioxoisoindolin-2-yl)1-methylsulfanylcyclopropanecarboxylate (3.00 g, 10.4 mmol), 2,4-dichloropyrimidine (4.76 g, 31.3 mmol) and 2,4,5,6-tetra(9H-carbazol-9-yl)isophthalonitrile (250 mg, 0.314 mmol) were dissolved in dimethylsulfoxide (120 mL). The solution was sparge-degassed with nitrogen for 10 min, then N,N-diisopropylethylamine (0.370 mL, 2.12 mmol) was added to the solution. The resulting solution was pumped through a flow cell (heated to 50° C.), which was irradiated with blue visible light. When the reaction setup had reached steady-state, a sample of the crude reaction mixture (68.5 g) was collected. The resulting solution was added drop wise to a mixture of water (50 mL) and heptane (50 mL), then a further portion of heptane (50 mL) was added and the mixture was stirred at approximately 20° C. for 30 min. The resulting precipitate was removed by filtration. The biphasic filtrate was transferred to a separating funnel and the organic layer was separated and concentrated under reduced pressure. The residue was purified by flash chromatography on silica gel, using an increasingly polar mixture of ethyl acetate in heptane as eluent. The fractions containing the desired product were then concentrated under reduced pressure to yield 2,4-dichloro-6-(1-methylsulfanylcyclopropyl)pyrimidine as a white solid (470 mg, 97% w/w, 1.98 mmol, 39% yield). $^1$H NMR (500 MHz, DMSO, 27° C.) 1.42-1.55 (2H, m), 1.61-1.77 (2H, m), 2.14 (3H, s), 8.03 (1H, s). MS: (M+H)$^+$ 235.

An alternative synthesis route is described below using the photo-catalyst 2,4,6-tris(diphenylamino)-3,5-difluorobenzonitrile (3DPA2FBN).

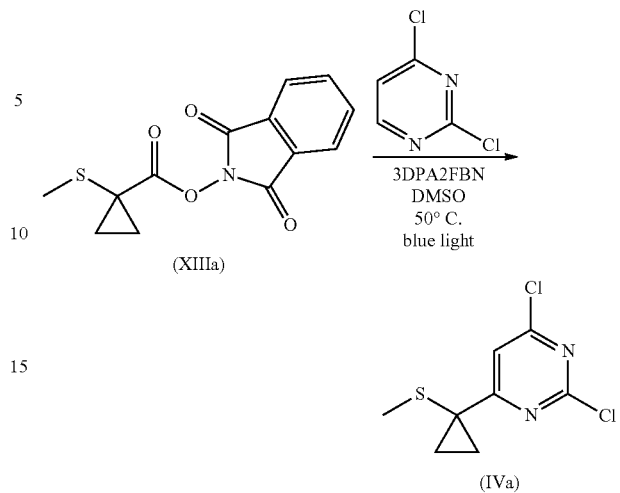

(1,3-Dioxoisoindolin-2-yl)1-methylsulfanylcyclopropanecarboxylate (250 g, 1.0 equiv.), 2,4-dichloropyrimidine (336.12 g, 2.50 equiv.) and 2,4,6-tris(diphenylamino)-3,5-difluorobenzonitrile (3DPA2FBN) (5.77 g, 0.01 equiv.) were dissolved in DMSO (6.25 L). The solution was sparge-degassed with nitrogen for 10 minutes. The resulting solution was pumped through plug-flow cell (FEP tubing, 8 mm internal diameter, heated to 50° C.), which was irradiated with blue light (450 nm). The output solution was added drop wise to a stirred mixture of water (3.12 L) and heptane (6.25 L). The layers were partitioned, then the organic layer was washed 3 times with a mixture of water (3.75 L) and DMSO (5.625 L). The organic layer was concentrated to yield 2,4-dichloro-6-[1-(methylsulfanyl)cyclopropyl]pyrimidine (118 g, 44% yield). Assay 79% w/w. $^1$H NMR (500 MHz, DMSO, 27° C.) 1.42-1.55 (2H, m), 1.61-1.77 (2H, m), 2.14 (3H, s), 8.03 (1H, s). MS: (M+H)$^+$ 235. Alternative benzonitrile photo-catalysts, isophthalonitrile photo-catalysts or other photo-catalysts could be used in place of the 3DPA2FBN catalyst described above and a person skilled in the art could adapt the photoredox reaction accordingly. It is possible to substitute the 3DPA2FBN photo-catalyst in the above photoredox reaction with a 2,3,4,5,6-pentakis(3,6-diphenylcarbazol-9-yl)benzonitrile photo-catalyst or a 2,4,6-tris(di-4-biphenylylamino)-3,5-difluorobenzonitrile photo-catalyst. The syntheses of these photo-catalysts are described below.

Example 13a: Preparation of the Photo-Catalyst 2,4,6-tris(diphenylamino)-3,5-difluorobenzonitrile (3DPA2FBN)

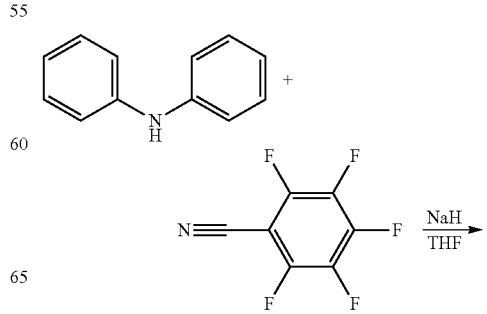

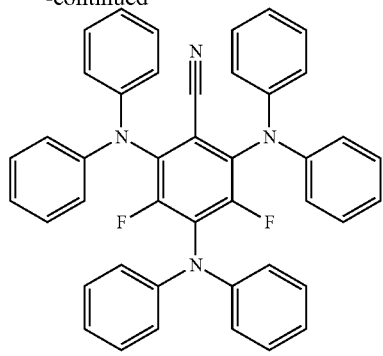

Sodium hydride (60% dispersion in mineral oil, 2.46 g) was added portion wise to a stirred solution of diphenylamine (6.57 g. 38.5 mmol) in tetrahydrofuran (80 mL) at approximately 20° C. The resulting mixture was heated to 50° C. for 1 hour. Pentafluorobenzonitrile (2.00 g, 10.3 mmol) was added, and the resulting mixture was heated at approximately 55° C. for 20 hours. The mixture was cooled to approximately 25° C. then water (2 mL) was added drop wise. Dichloromethane (200 mL) and water (150 mL) were added, then the layers were partitioned. The organic layer was washed with water (150 mL) then concentrated. The residue was purified by flash chromatography (eluent isohexane/DCM). The product was slurried in methanol then collected by filtration and dried to yield 2,4,6-tris(diphenylamino)-3,5-difluorobenzonitrile (3.89 g, 6.01 mmol, 59%) as a yellow solid. $^1$H NMR (500 MHz, DMSO, 27° C.) 6.88-7.17 (18H, m), 7.20-7.37 (12H, m). MS: (M+H)$^+$ 641.

Example 13b: Preparation of the Photo-Catalyst 2,3,4,5,6-pentakis(3,6-diphenylcarbazol-9-yl)benzonitrile

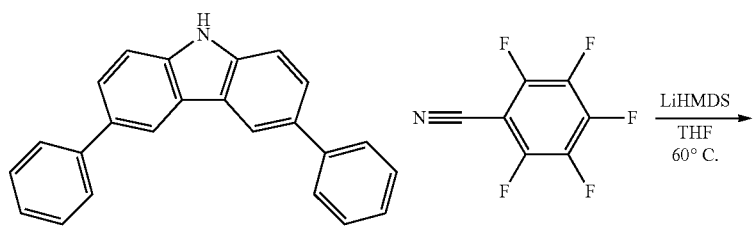

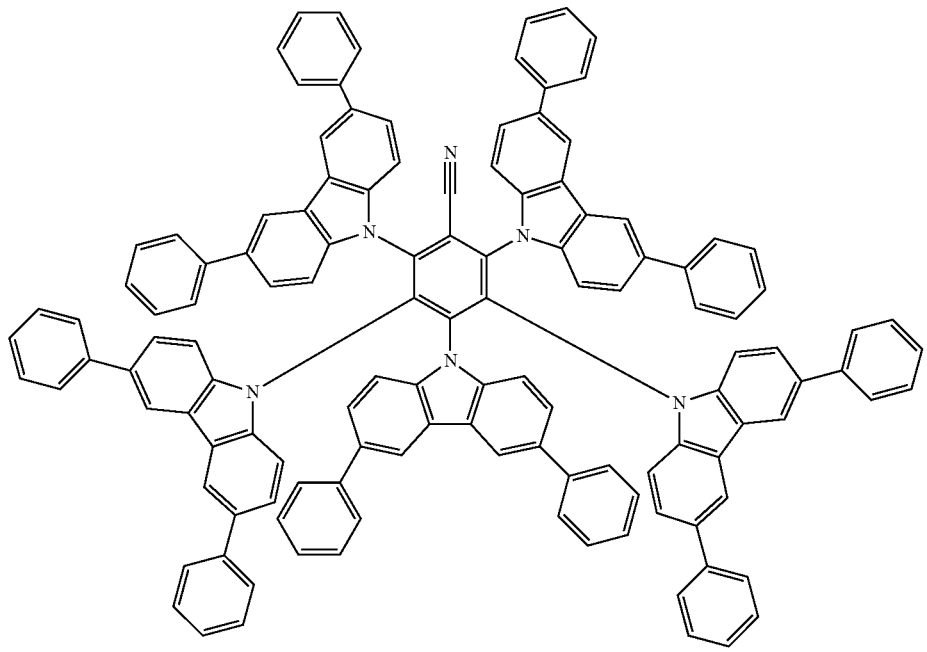

Sodium hydride (60% dispersion in mineral oil, 0.400 g) was added portion wise to a stirred solution of 3,6-diphenyl-9H-carbazole (2.15 g, 6.73 mmol), in tetrahydrofuran (20 mL) at approximately 20° C. The resulting mixture was stirred at 20° C. for 1 hour. Pentafluorobenzonitrile (0.200 g, 1.05 mmol) was added, and the resulting mixture was stirred at approximately 55° C. for 3 days. Water (20 mL) and dichloromethane (100 mL) were added then the layers were partitioned. The organic layer was washed with brine (20 mL) then concentrated. The residue was purified by flash chromatography using heptane/DCM as eluent to yield e2,3,4,5,6-pentakis(3,6-diphenylcarbazol-9-yl)benzonitrile (350 mg, 0.2071 mmol, 20%) as a solid. $^1$H NMR (500 MHz, DMSO, 27° C.) 7.04-7.11 (6H, m), 7.22-7.44 (42H, m), 7.54-7.57 (4H, m), 7.64-7.68 (8H, m), 7.82-7.52 (6H, m), 7.90-7.94 (4H, m), 7.96-7.99 (2H, m), 8.07-8.11 (4H, m), 8.34 (4H, m).

Example 13c: Preparation of the Photo-Catalyst 2,4,6-tris(di-4-biphenylylamino)-3,5-difluorobenzonitrile

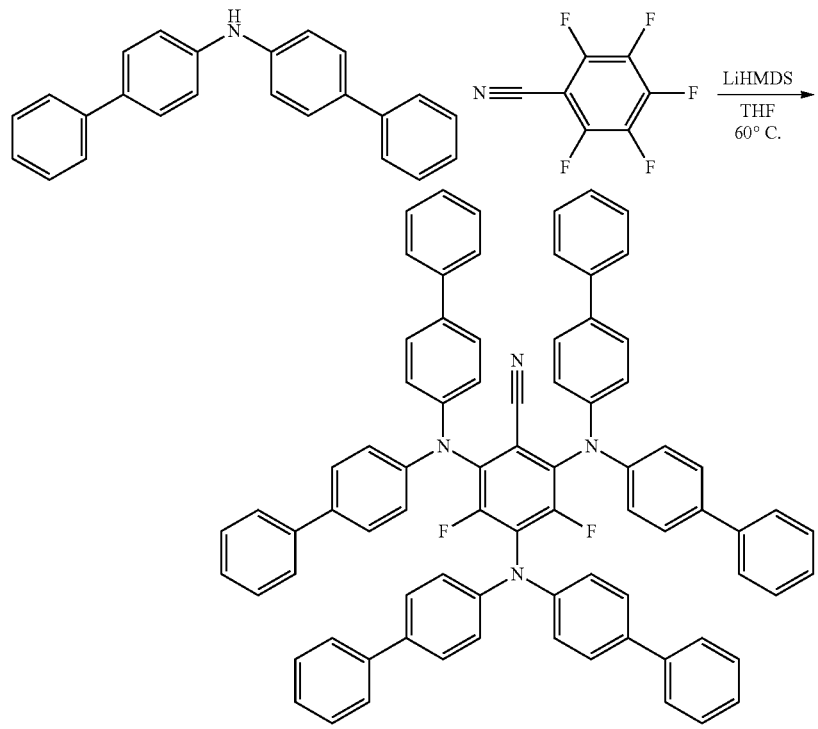

Lithium bis(trimethylsilyl)amide (LOM solution in THF, 6.15 mL) was added to a solution of bis(4-biphenylyl)amine (1.77 g, 5.38 mmol) in tetrahydrofuran (9.00 mL) at 20° C. After 10 minutes of stirring at 20° C., pentafluorobenzonitrile (0.300 g, 1.54 mmol) was added. The resulting mixture was stirred at 60° C. for 20 hours. The mixture was cooled to 20° C. then water (1.5 mL) was added then the mixture was concentrated. The residue was chromatographed using dichloromethane/heptane as eluent. The resulting product was slurried with ethyl acetate/heptane and isolated by filtration then dried to yield 2,4,6-tris(di-4-biphenylylamino)-3,5-difluorobenzonitrile (0.303 g, 0.276 mmol, 18%) as a solid. $^1$H NMR (500 MHz, DMSO, 27° C.) 7.24-7.46 (30H, m), 7.55-7.72 (24H, m). MS: (M+H)$^+$ 1098.

The invention claimed is:
1. A process for preparing a compound of Formula (II):

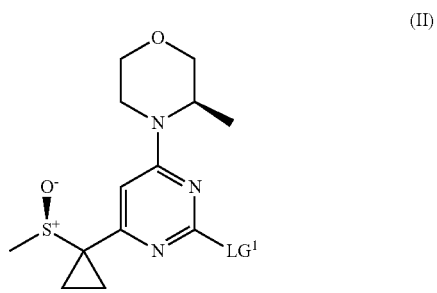

comprising reacting a compound of Formula (III):

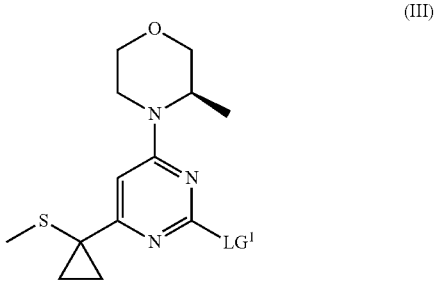

with an oxidative enzyme, wherein LG¹ is selected from the group consisting of chlorine, bromine, and triflate.

2. The process of claim 1, wherein the compound of Formula (III) is prepared by reacting a compound of Formula (IV):

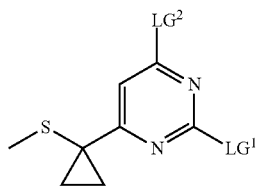
(IV)

with (R)-3-methylmorpholine or a salt thereof, wherein LG¹ and LG² are independently selected from the group consisting of chlorine, bromine, and triflate.

3. The process of claim 2, wherein the compound of Formula (IV) is prepared by reacting a compound of Formula (V):

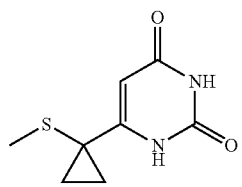
(V)

with an activating reagent.

4. The process of claim 3, wherein the compound of Formula (V) is prepared from a compound of Formula (VI):

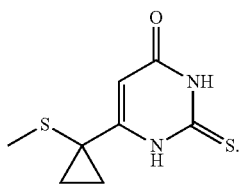
(VI)

5. The process of claim 4, wherein the compound of Formula (VI) is prepared by reacting a compound of Formula (VII):

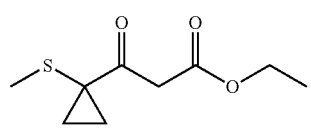
(VII)

with thiourea.

6. The process of claim 5, wherein the compound of Formula (VII) is prepared by acylation of a malonate derivative with an activated form of a compound of Formula (VIII):

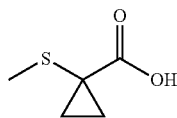
(VIII)

followed by decarboxylation.

7. The process of claim 6, wherein the compound of Formula (VIII) is prepared by the thiomethylation and base-induced cyclisation of a compound of Formula (IX):

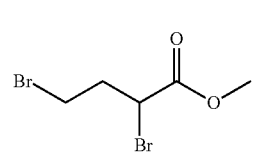
(IX)

followed by hydrolysis.

8. The process of claim 2, wherein the compound of Formula (IV) is prepared by reacting a compound of Formula (XIII):

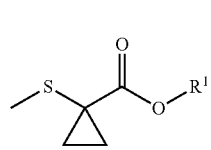
(XIII)

with a 2,4-difunctionalised pyrimidine in the presence of light and a photo-catalyst, wherein R¹ is a phthalimide or tetrachlorophthalimide group.

9. The process of claim 8, wherein the compound of Formula (XIII) is prepared by reacting a compound of Formula (VIII):

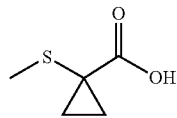
(VIII)

with OH—R¹, wherein R¹ is a phthalimide or tetrachlorophthalimide group.

10. A compound, or a salt thereof, selected from the group consisting of:
a compound of Formula (II):

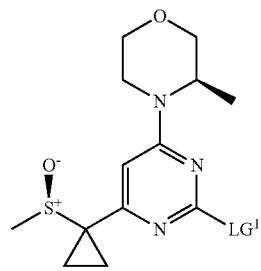
(II)

wherein LG¹ is bromine or triflate;

a compound of Formula (III):

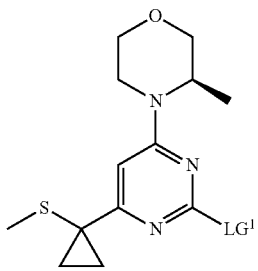

(III)

wherein LG¹ is selected from the group consisting of chlorine, bromine, and triflate;

a compound of Formula (IV):

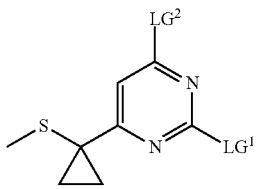

(IV)

wherein LG¹ and LG² are independently selected from the group consisting of chlorine, bromine, and triflate;

a compound of Formula (V):

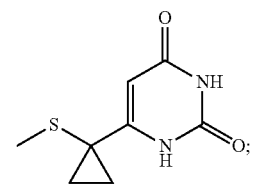

(V)

a compound of Formula (VI):

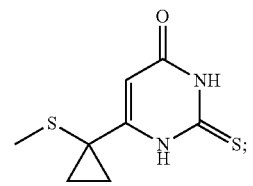

(VI)

a compound of Formula (VII):

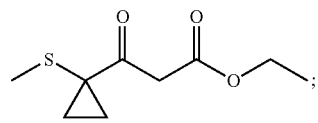

(VII)

a compound of Formula (XIIb):

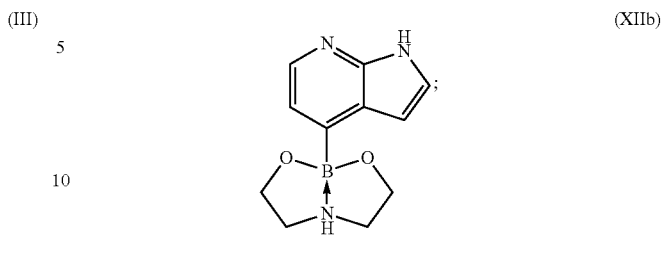

(XIIb)

and salts thereof.

11. The compound of claim 10, wherein LG¹ is chlorine for the compound of Formula (III), and LG¹ and LG² are each chlorine for the compound of Formula (IV).

12. A process for preparing a compound of Formula (I):

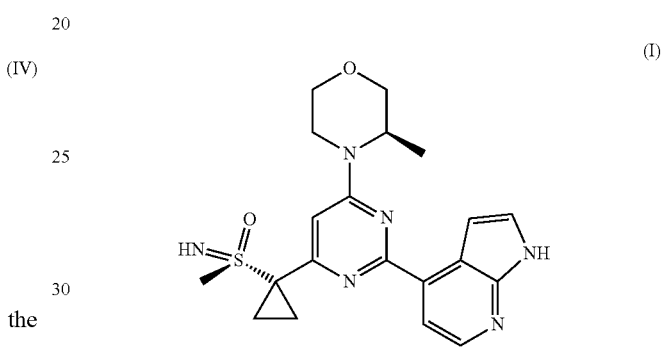

(I)

or a salt thereof,
wherein the process comprises the following steps:
reacting a compound of Formula (III):

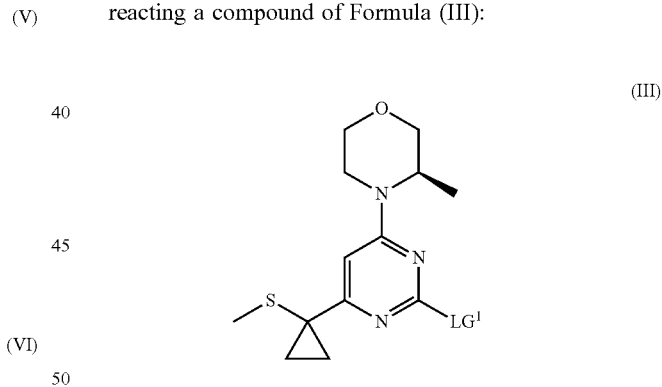

(III)

with an oxidising enzyme to form a compound of Formula (II):

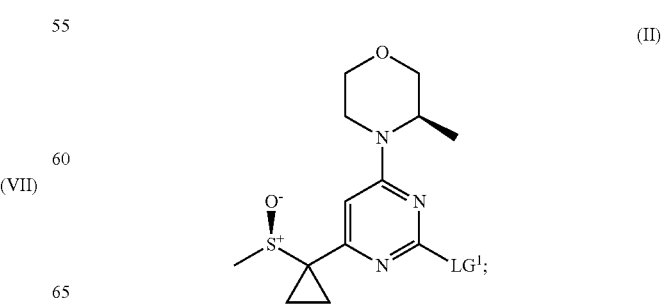

(II)

reacting the compound of Formula (II) with a nitrogen source followed by iodobenzene diacetate to form a compound of Formula (X):

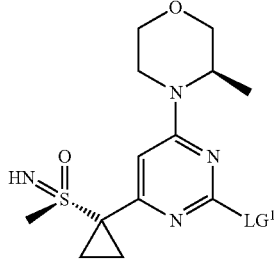

(X)

or salt thereof;

reacting a compound of Formula (XI):

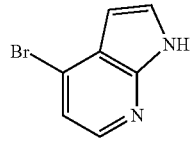

(XI)

with a boron reagent in the presence of a palladium catalyst to form a compound of Formula (XII):

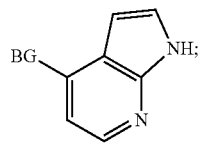

(XII)

and reacting the compound of Formula (X), or salt thereof, with the compound of Formula (XII) to form the compound of Formula (I), or a pharmaceutically acceptable salt thereof;

wherein $LG^1$ is selected from the group consisting of chlorine, bromine, and triflate, and BG is a boronate ester.

13. The process of claim 12, wherein the step to form the compound of Formula (XI) further comprises the addition of diethanolamine after reaction with a boron reagent in the presence of a palladium catalyst.

14. The process of claim 13, wherein the compound of Formula (XII) is a compound of Formula (XIIb):

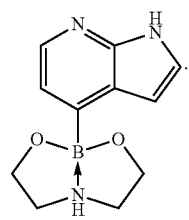

(XIIb)

15. A process for preparing a compound of Formula (I):

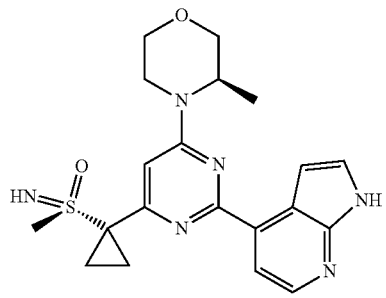

(I)

or a salt thereof, wherein the process comprises reacting a compound of Formula (XI):

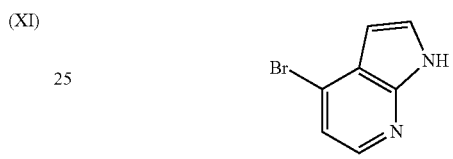

(XI)

with a boron reagent in the presence of a palladium catalyst followed by the addition of diethanolamine to form a compound of Formula (XIIb):

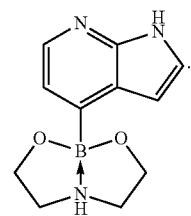

(XIIb)

16. The process of claim 12, further comprising the steps:

(a) cyclopropanating a compound of Formula (IX):

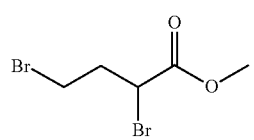

(IX)

followed by hydrolysis to form a compound of Formula (VIII):

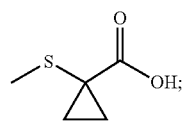

(VIII)

(b) reacting the compound of Formula (VIII) with an acylating agent to form a compound of Formula (VII):

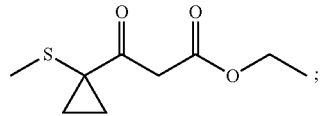
(VII)

(c) reacting the compound or formula (VII) with urea or thiourea to form a compound of Formula (VI):

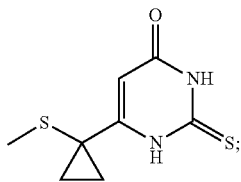
(VI)

(d) reacting the compound of Formula (VI) with a suitable reagent to form a compound of Formula (V):

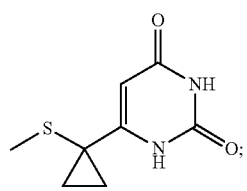
(V)

(e) reacting the compound of Formula (V) with an activating reagent to form a compound of Formula (IV):

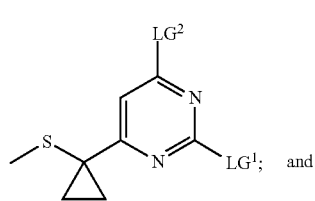
(IV)

(f) coupling the compound of Formula (IV) with (R)-3-methylmorpholine, or a salt thereof, to form a compound of Formula (III):

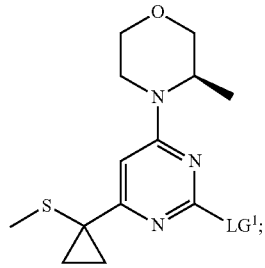
(III)

wherein $LG^1$ and $LG^2$ are each independently selected from the group consisting of chlorine, bromine, and triflate.

17. The process of claim 12, further comprising the steps:

(a) cyclopropanating a compound of Formula (IX);

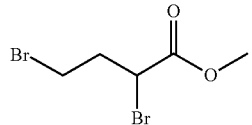
(IX)

followed by hydrolysis to form a compound of Formula (VIII):

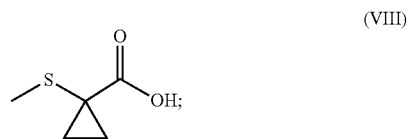
(VIII)

(b) reacting the compound of Formula (VIII) with $R^1$—OH to form a compound of Formula (XIII):

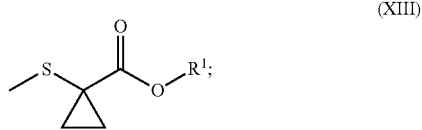
(XIII)

(c) reacting the compound of Formula (XIII) with a 2,4-difunctionalised pyrimidine in the presence of light and a photo-catalyst to form a compound of Formula (IV):

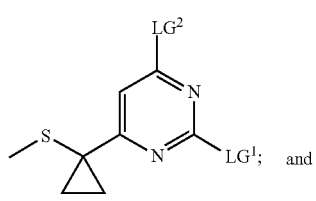
(IV)

(d) coupling the compound of Formula (IV) with (R)-3-methylmorpholine, or a salt thereof, to form a compound of Formula (III):

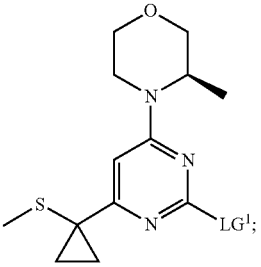
(III)

wherein $R^1$ is a phthalimide or tetrachlorophthalimide group, and $LG^1$ and $LG^2$ are independently selected from the group consisting of chlorine, bromine, and triflate.

18. The process of claim 16, wherein $LG^1$ and $LG^2$ are both chlorine.

19. The process of claim 1, wherein $LG^1$ is chlorine.

20. The process of claim 2, wherein $LG^1$ and $LG^2$ are both chlorine.

21. The process of claim 12, wherein the boron reagent is bis(pinacolato)diboron.

22. The process of claim 17, wherein $LG^1$ and $LG^2$ are both chlorine.

* * * * *